(12) United States Patent
Cawello et al.

(10) Patent No.: US 11,389,410 B2
(45) Date of Patent: *Jul. 19, 2022

(54) MULTI-DAY PATCH FOR THE TRANSDERMAL ADMINISTRATION OF ROTIGOTINE

(71) Applicant: LTS Lohmann Therapie-Systeme AG, Andernach (DE)

(72) Inventors: Willi Cawello, Monheim (DE); Aurelia Lappert, Woluwe Saint Pierre (BE); Kristina Kassner, Bergisch Gladbach (DE); Hans-Michael Wolff, Monheim (DE); Walter Müller, Andernach (DE); Johannes Josef Leonhard, Bendorf (DE); Marco Emgenbroich, Rheinbach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/443,210

(22) PCT Filed: Nov. 21, 2013

(86) PCT No.: PCT/EP2013/003515
§ 371 (c)(1),
(2) Date: May 15, 2015

(87) PCT Pub. No.: WO2014/079573
PCT Pub. Date: May 30, 2014

(65) Prior Publication Data
US 2015/0290142 A1    Oct. 15, 2015

(30) Foreign Application Priority Data

Nov. 22, 2012    (EP) .................................... 12193808

(51) Int. Cl.
*A61K 9/70*    (2006.01)
*A61K 31/381*    (2006.01)
*B32B 37/12*    (2006.01)

(52) U.S. Cl.
CPC .......... *A61K 9/7092* (2013.01); *A61K 9/7069* (2013.01); *A61K 9/7084* (2013.01);
(Continued)

(58) Field of Classification Search
None
See application file for complete search history.

(56) References Cited

U.S. PATENT DOCUMENTS 4,769,028 A * 9/1988 Hoffmann ............ A61K 9/7092
424/443
4,814,168 A 3/1989 Sablotsky et al.
(Continued)

FOREIGN PATENT DOCUMENTS

CA    2374930 A1    1/2001
CN    1462185 A    12/2003
(Continued)

OTHER PUBLICATIONS

International Preliminary Report on Patentability issued in International Application No. PCT/EP2013/003515 dated May 26, 2015, 5 pages.
(Continued)

*Primary Examiner* — Isis A Ghali
(74) *Attorney, Agent, or Firm* — ProPat, LLC; Cathy R. Moore

(57) ABSTRACT

The present invention relates to a transdermal therapeutic system, comprising (a) a backing layer, (b) a solvent-based self-adhesive matrix layer containing rotigotine as active ingredient, and (c) a release liner, wherein the self-adhesive matrix layer has a coating weight of about 75-400 g/m² and
(Continued)

comprises a reservoir layer containing about 9-25 wt.-% rotigotine based on the weight of the reservoir layer, a kit comprising two transdermal therapeutic systems of the present invention as well as a method for the preparation of the transdermal therapeutic system of the present invention. In addition, the present invention relates to a transdermal therapeutic system comprising rotigotine as active ingredient for use in the treatment of patients suffering from Parkinson's disease, Parkinson's plus syndrome, depression, fibromyalgia and the restless-legs syndrome and for use in the treatment or prevention of dopaminergic neuron loss or cognitive disorders by transdermal administration of rotigotine once or twice weekly, wherein the transdermal therapeutic system comprises a backing layer, a solvent-based rotigotine containing self-adhesive matrix layer as well as a release liner and is adapted to allow for the transdermal administration of therapeutically effective amounts of rotigotine for at least 3 days.

27 Claims, 11 Drawing Sheets

(52) U.S. Cl.
CPC ............ *A61K 31/381* (2013.01); *B32B 37/12* (2013.01); *B32B 2556/00* (2013.01)

(56) References Cited

U.S. PATENT DOCUMENTS

| | | | |
|---|---|---|---|
| 4,994,267 A | 2/1991 | Sablotsky | |
| 4,994,278 A | 2/1991 | Sablotsky | |
| 5,032,207 A | 7/1991 | Sablotsky et al. | |
| 5,300,291 A | 4/1994 | Sablotsky et al. | |
| 5,405,486 A | 4/1995 | Sablotsky et al. | |
| 5,474,783 A | 12/1995 | Miranda et al. | |
| 5,656,285 A | 8/1997 | Sablotsky et al. | |
| 5,656,286 A | 8/1997 | Miranda et al. | |
| 5,686,099 A | 11/1997 | Sablotsky et al. | |
| 5,719,197 A | 2/1998 | Kanios et al. | |
| 5,958,446 A | 9/1999 | Miranda et al. | |
| 6,024,976 A | 2/2000 | Miranda et al. | |
| 6,221,383 B1 | 4/2001 | Miranda et al. | |
| 6,235,306 B1 | 5/2001 | Miranda et al. | |
| 6,884,434 B1* | 4/2005 | Muller | A61K 9/7061 424/448 |
| 7,383,083 B2 | 6/2008 | Fischer et al. | |
| 7,847,014 B2 | 12/2010 | Koch et al. | |
| 8,211,462 B2 | 7/2012 | Breitenbach et al. | |
| 8,246,979 B2 | 8/2012 | Schacht et al. | |
| 9,265,752 B2 | 2/2016 | Wang et al. | |
| 2001/0053383 A1 | 12/2001 | Miranda et al. | |
| 2003/0026830 A1* | 2/2003 | Lauterback | A61K 31/381 424/449 |
| 2003/0060479 A1 | 3/2003 | Brown et al. | |
| 2003/0149394 A1 | 8/2003 | Joshi | |
| 2003/0198622 A1 | 10/2003 | Van Osdol et al. | |
| 2004/0131897 A1 | 7/2004 | Jenson et al. | |
| 2004/0137045 A1 | 7/2004 | Breitenbach et al. | |
| 2004/0138299 A1 | 7/2004 | Cahill et al. | |
| 2004/0234583 A1* | 11/2004 | Muller | A61P 29/00 424/449 |
| 2005/0019385 A1* | 1/2005 | Houze | A61K 9/7069 424/449 |
| 2005/0175678 A1* | 8/2005 | Breitenbach | A61K 31/381 424/448 |
| 2005/0202073 A1 | 9/2005 | Jackson et al. | |
| 2005/0260254 A1 | 11/2005 | Breitenbach et al. | |
| 2006/0263419 A1 | 11/2006 | Wolff | |
| 2009/0048556 A1 | 2/2009 | Durand | |
| 2009/0299304 A1 | 12/2009 | Tang | |
| 2010/0119585 A1 | 5/2010 | Hille et al. | |
| 2010/0286590 A1 | 11/2010 | Durand | |
| 2010/0311661 A1 | 12/2010 | Küllertz et al. | |
| 2011/0027345 A1 | 2/2011 | Wang et al. | |
| 2011/0104244 A1 | 5/2011 | Hille et al. | |
| 2014/0046279 A1 | 2/2014 | Leonhard et al. | |
| 2015/0290142 A1 | 10/2015 | Cawello et al. | |

FOREIGN PATENT DOCUMENTS

| | | |
|---|---|---|
| CN | 1 606 435 A | 4/2005 |
| CN | 1671375 A | 9/2005 |
| CN | 1897935 A | 1/2007 |
| CN | 101146524 A | 3/2008 |
| CN | 101601664 A | 12/2009 |
| CN | 102458397 A | 5/2012 |
| CN | 102770128 A | 11/2012 |
| DE | 10 2012 013 421 A1 | 1/2014 |
| EP | 1 669 063 A1 | 6/2006 |
| EP | 2177217 A1 | 4/2010 |
| EP | 2292219 A1 | 3/2011 |
| JP | 1998509621 A | 9/1998 |
| JP | 2003-526656 A | 9/2003 |
| JP | 2004-521085 A | 7/2004 |
| JP | 2004-525164 A | 8/2004 |
| JP | 2004-528359 A | 9/2004 |
| JP | 2005-528425 A | 9/2005 |
| JP | 2005-535686 A | 11/2005 |
| JP | 2005-535687 A | 11/2005 |
| JP | 2006-508908 A | 3/2006 |
| JP | 2006515952 A | 6/2006 |
| JP | 2006178807 A | 7/2006 |
| JP | 2007-528392 A | 10/2007 |
| JP | 2009297808 A | 12/2009 |
| JP | 2010-106037 A | 5/2010 |
| JP | 2010158554 A | 7/2010 |
| JP | 2010536434 A | 12/2010 |
| JP | 2011-500647 A | 1/2011 |
| JP | 2011-504902 A | 2/2011 |
| JP | 2011-526592 A | 10/2011 |
| JP | 2012501799 A | 1/2012 |
| JP | 2012-504609 A | 2/2012 |
| JP | 2012-509276 A | 4/2012 |
| JP | 2013-510805 A | 3/2013 |
| JP | 2013-515041 A | 5/2013 |
| WO | 89/10108 A1 | 11/1989 |
| WO | 91/14463 A1 | 10/1991 |
| WO | 92/19451 A1 | 11/1992 |
| WO | 93/00058 A1 | 1/1993 |
| WO | 95/18603 A1 | 7/1995 |
| WO | 99/49582 A2 | 9/1999 |
| WO | 99/49852 A1 | 10/1999 |
| WO | 2000/44437 A1 | 8/2000 |
| WO | 2001/01967 A1 | 1/2001 |
| WO | 2002/015903 A2 | 2/2002 |
| WO | 2002/089777 A1 | 11/2002 |
| WO | 2003/015678 A1 | 2/2003 |
| WO | 2003/092677 A1 | 11/2003 |
| WO | 2004/012721 A2 | 2/2004 |
| WO | 2004/012730 A1 | 2/2004 |
| WO | 2004/050083 A1 | 6/2004 |
| WO | 2005/009424 A1 | 2/2005 |
| WO | 2005/063236 A1 | 7/2005 |
| WO | 2005/063237 A1 | 7/2005 |
| WO | 2005/092331 A1 | 10/2005 |
| WO | 2005/119610 A1 | 12/2005 |
| WO | 2008/061639 A1 | 5/2008 |
| WO | 2009/068520 A2 | 6/2009 |
| WO | 2010/042152 A2 | 4/2010 |
| WO | WO-2011057714 A2 * | 5/2011 ........... A61K 9/7007 |
| WO | 2011/076879 A1 | 6/2011 |
| WO | 2012/071175 A1 | 5/2012 |
| WO | 2012/084969 A1 | 6/2012 |
| WO | 2013/075822 A1 | 5/2013 |
| WO | 2013/075823 A1 | 5/2013 |
| WO | 2013/088254 A1 | 6/2013 |

(56) References Cited

FOREIGN PATENT DOCUMENTS

WO     2014/079573 A1    5/2014
WO     2014/195352 A1    12/2014

OTHER PUBLICATIONS

International Search Report of PCT/EP2013/003515 dated Jan. 8, 2014, 2 pages.
Chinese Search Report for the corresponding CN Application 201380054953.X, 6 pages.
Henkel Corporation, "DURO-TAK and GELVA Transdermal Pressure Sensitive Adhesives," Product Selection Guide, Sep. 2013.
Dow Corning: Amine-Compatible Silicone Adhesives, Jul. 28, 2008.
Fachinformation Neupro (Aug. 2011) with English Translation.
Kandavilli, Sateesh et al., "Polymers in Transdermal Drug Delivery Systems," Pharmaceutical Technology, May 2002, pp. 62-80.
www.ucb.com/investors/Our-equity-story/Neupro(Jan. 6, 2016).
H.F. Hammond in D. Satas "Handbook of Pressure Sensitive Adhesive Techology" (1989) 2nd ed., Chapter 4, Van Nostrand Reinhold, New York, p. 38.
"Pressure Sensitive Tack of Adhesives Using an Inverted Probe Machine" ASTM D2979-71 (1982).
3. K.L. Ulman and R.P. Sweet, "The Correlation of Tape Properties and Rheology" (1998), Information Brochure, Dow Corning Corp., USA.
Dow Corning 360 Medical Fluid, (retrieved from on-line website; https://www.b2bcomposites.com/msds/ted/71115.pdf, pp. 1-7, 2010).
Chien, "Developmental Concepts and Practice in Transdermal Therapeutic Systems," Chapter 2 in Transdermal Controlled Systemic Medications, 1987, vol. 31, pp. 25-44.
Office Actions in U.S. Appl. No. 14/975,478, dated Mar. 24, 2017 and Oct. 5, 2017. (parent to U.S. Appl. No. 16/009,613).
Office Actions in U.S. Appl. No. 15/312,433, dated Jul. 18, 2019 and Mar. 23, 2020.
Office Actions in U.S. Appl. No. 15/312,509, dated Jan. 16, 2018; Jul. 27, 2018; Jul. 11, 2019; and Apr. 15, 2020.
Office Actions in U.S. Appl. No. 15/312,542, dated Dec. 22, 2017, Jul. 17, 2018, Dec. 27, 2018, Jun. 18, 2019 and Nov. 20, 2019.
Office Actions in U.S. Appl. No. 16/009,613, dated Dec. 20, 2018 and Nov. 7, 2019.
JP Application No. 2018-147720 First Office Action, which corresponds to U.S. Appl. No. 16/009,613.
JP Application No. 2016-522618 First Office Action, which corresponds to U.S. Appl. No. 16/009,613.
JP Application No. 2016-522618 Second Office Action, which corresponds to U.S. Appl. No. 16/009,613.
Office Actions in U.S. Appl. No. 16/009,613, dated May 22, 2020.
Office Actions in U.S. Appl. No. 15/312,509 dated Dec. 28, 2020.
Office Actions in U.S. Appl. No. 15/312,433, dated Oct. 21, 2020.
Office Actions in U.S. Appl. No. 15/513,542, dated Jun. 26, 2020.
International Search Report, PCT/EP2015/061099, which corresponds to U.S. Appl. No. 15/312,509, filed Nov. 18, 2016.
International Search Report PCT/EP2015/061112, which corresponds to U.S. Appl. No. 15/312,433, filed Nov. 18, 2016.
International Preliminary Report on Patentability, PCT/EP2014/064166, which corresponds to U.S. Appl. No. 14/975,478, filed Dec. 18, 2015.

* cited by examiner

Example 1 (API : PVP 9:2)

Example 2 (API : PVP 18:4)

Example 3 (API : PVP 18:8)

Example 4, 8, 9 (API : PVP 18:8)

Example 5, 6 (API : PVP 9:4)

Example 7 (API : PVP 9:4) / (API : PVP 18:8)

MULTI-DAY PATCH FOR THE TRANSDERMAL ADMINISTRATION OF ROTIGOTINE

This application is a US national phase of International Application No. PCT/EP2013/003515 filed on Nov. 21, 2013, which claims priority to European Patent Application No. 12193808.8 filed on Nov. 22, 2012.

FIELD OF THE INVENTION

The present invention relates to a novel multi-day transdermal therapeutic system (TTS), which is adapted to allow for the transdermal administration of therapeutically effective amounts of rotigotine for at least 3 days and up to at least 7 days.

TECHNICAL BACKGROUND

Rotigotine is the International Non-Proprietary Name (INN) of the compound (−)-5,6,7,8-tetrahydro-6-[propyl-[2-(2-thienyl)ethyl]-amino]-1-naphthalenol having the structure shown below

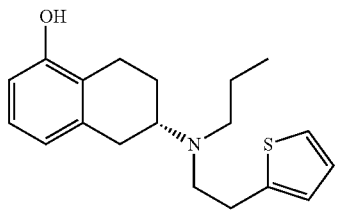 [SMILES: CCCN(CCc1cccs1)[C@H]1CCc2c(O)cccc2C1]

Rotigotine exists in two different polymorphic states, Polymorphic Form I and Polymorphic Form II, which can be differentiated by their melting point, infrared (IR) spectroscopy, solid state nuclear magnetic resonance (SSNMR) or Raman spectroscopy as well as differential scanning calorimetry (DSC) and X-ray powder diffraction (XRD). The different physicochemical characteristics of the two polymorphic forms of rotigotine are for example described in WO 2009/068520.

Rotigotine is a non-ergolinic dopamine D1/D2/D3-receptor agonist that resembles dopamine structurally and has a similar receptor profile but a higher receptor affinity.

In contrast to other non-ergolinic dopamine agonists, rotigotine has significant D1 activity, which may contribute to a greater physiological action.

In contrast to ergolinic compounds, rotigotine has a very low affinity for 5 $HT_{2B}$ receptors and thus a low risk of inducing fibrosis.

Actions on non-dopaminergic receptors (such as 5-$HT_{1A}$ agonism and $A_{2B}$ antagonism) may contribute to other beneficial effects, such as antidyskinetic activity, neuroprotective activity and antidepressive effects.

Rotigotine is disclosed as active agent for treating patients suffering from Parkinson's disease (described in WO 2002/089777), Parkinson's plus syndrome (described in WO 2005/092331), depression (described in WO 2005/009424) and the restless-legs syndrome (described in WO 2003/092677) as well as for the treatment or prevention of dopaminergic neuron loss (described in WO 2005/063237).

Known pharmaceutical compositions containing rotigotine comprise a single-day, solvent-based transdermal therapeutic system (TTS) (described in WO 99/49852), a depot form (described in WO 02/15903), an iontophoretic device (described in WO 2004/050083) and an intranasal formulation (described in WO 2005/063236).

In WO 2004/012721, a transdermal therapeutic system (TTS) is described, which contains rotigotine in a self-adhesive layer being prepared from a hot-meltable adhesive. The transdermal therapeutic systems of WO 2004/012721 are provided for a single-day or a multi-day application and allow for a continuous release of rotigotine for e.g. up to at least 7 days in an in vitro skin permeation model.

Compared to the hot-meltable adhesive-based transdermal therapeutic systems of WO 2004/012721, the solvent-based transdermal therapeutic systems known from the prior art have a limited capacity for loading their self-adhesive layer with rotigotine.

So far, it was therefore not possible to prepare solvent-based transdermal therapeutic systems providing for a continuous release of rotigotine for 3 or more days.

It was, therefore, an object of the present invention to provide a solvent-based transdermal therapeutic system comprising rotigotine in an amount allowing for the continuous administration of therapeutically effective amounts of rotigotine for at least 3 days and up to at least 7 days after one application.

SUMMARY OF THE INVENTION

The present invention is based on the development of solvent-based self-adhesive matrices for transdermal therapeutic systems containing increased amounts of rotigotine, which allow for the transdermal administration of therapeutically effective amounts of rotigotine for at least 3 days and up to at least 7 days after one application of a corresponding transdermal therapeutic system and wherein the transdermal therapeutic system complies with the needs of a convenient application in view of size, thickness and skin tolerance and can easily and cost-effectively be prepared.

Moreover, it was surprisingly found that the total amount of rotigotine being required for the continuous administration of therapeutically effective amounts of rotigotine for at least 3 days and up to at least 7 days by the transdermal therapeutic system of the present invention was lower than expected/calculated for the respective number of single-day solvent-based transdermal therapeutic systems known from the prior art.

In a first aspect, the present invention therefore provides a transdermal therapeutic system, comprising
 (a) a backing layer,
 (b) a solvent-based self-adhesive matrix layer containing rotigotine as active ingredient, and
 (c) a release liner,
wherein the self-adhesive matrix layer has a coating weight of about 75-400 g/m² and comprises a reservoir layer containing about 9-25 wt.-% rotigotine based on the weight of the reservoir layer.

In a further embodiment the transdermal therapeutic system, comprising
 (a) a backing layer,
 (b) a solvent-based self-adhesive matrix layer containing rotigotine as active ingredient, and
 (c) a release liner,
wherein the self-adhesive matrix layer has a coating weight of about 100-400 g/m² and comprises a reservoir layer containing about 9-20 wt.-% rotigotine based on the weight of the reservoir layer.

In the context of the present application the term "about" shall mean+/−10% of the respective figure unless otherwise indicated.

In one embodiment, the self-adhesive matrix layer of the transdermal therapeutic system further comprises a skin adhesive layer containing rotigotine in a concentration of about 0-10 wt.-% based on the weight of the skin adhesive layer and the skin adhesive layer is provided between the reservoir layer and the release liner and has a lower rotigotine concentration than the reservoir layer.

In a further embodiment, the reservoir layer of the transdermal therapeutic system has a coating weight of about 75-300 $g/m^2$, preferably of about 75-200 $g/m^2$, more preferably about 100-150 $g/m^2$ and contains about 9-25 wt.-% rotigotine, preferably about 18 wt.-% rotigotine based on the weight of the reservoir layer.

In a further embodiment, the reservoir layer of the transdermal therapeutic system has a coating weight of about 75-200 $g/m^2$, preferably of about 100-150 $g/m^2$ and contains about 9-25 wt.-% rotigotine, preferably about 18 wt.-% rotigotine based on the weight of the reservoir layer and the skin adhesive layer has a coating weight of about 10-150 $g/m^2$.

In a preferred embodiment, the skin adhesive layer of the transdermal therapeutic system has a coating weight of about 15-120 $g/m^2$ and contains about 5-10 wt.-% rotigotine based on the weight of the skin adhesive layer.

In a further preferred embodiment, the skin adhesive layer of the transdermal therapeutic system has a coating weight of about 15-50 $g/m^2$ and contains about 0-5 wt.-% rotigotine based on the weight of the skin adhesive layer.

In a further embodiment, the transdermal system contains about 10-32 mg rotigotine/10 $cm^2$ surface of the self-adhesive matrix layer, preferably about 27 mg rotigotine/10 $cm^2$ surface of the self-adhesive matrix layer.

In a preferred embodiment, the reservoir layer or the reservoir layer and the skin adhesive layer, if it contains rotigotine, of the transdermal therapeutic system further contain(s) polyvinylpyrrolidone and the rotigotine to polyvinylpyrrolidone weight ratio in the respective layer is 9:2 to 9:5, preferably 9:3 to 9:5, or multiples thereof.

In a further preferred embodiment, the reservoir layer and, if present, the skin adhesive layer of the transdermal therapeutic system each contain at least one, preferably two, amine-resistant silicone pressure sensitive adhesive(s).

In a further embodiment, the transdermal therapeutic system is adapted to allow for the transdermal administration of therapeutically effective amounts of rotigotine for at least 3-7 days.

In a preferred embodiment, the transdermal therapeutic system is adapted to allow for the transdermal administration of therapeutically effective amounts of rotigotine for at least 7 days.

The multi-day transdermal therapeutic system of the present invention has the advantage of allowing for a reduced application frequency compared to daily applied conventional transdermal therapeutic systems. This is particularly advantageous for patients suffering from severe dopaminergic disorders, like Parkinson's Disease, as these patients often experience motor disabilities which make the frequent handling and administration of transdermal patches difficult. At the same time, the number of skin application sites to be treated with patches during a long-term patch medication is reduced. A prolongation of the medication interval e.g. from 1 day to at least 3 or even at least 7 days minimizes the potential risk of skin lesions associated with repeated patch stripping from the patients' skin at skin application sites selected for repeated patch administration. In addition, the influence of inter- and intra-individually differing lag-times on the absorption of rotigotine, which may be associated with the daily replacement of rotigotine-containing patches in the case of low skin permeability and which may cause therapeutically unwanted fluctuations of the plasma levels of rotigotine, can be eliminated by the multi-day patches of the present invention. Finally, the replacement of a daily patch administration by one single administration for several days, for example by an administration once or twice weekly, contributes to the reduction of the costs of the respective medication by saving material and production time.

In a second aspect, the present invention provides a kit comprising two transdermal therapeutic systems of the present invention, wherein the two transdermal therapeutic systems may have the same or a different rotigotine content. In one embodiment, the two transdermal therapeutic systems of the kit have a different rotigotine content and one of them is adapted to allow for the transdermal administration of therapeutically effective amounts of rotigotine for at least 3 days and the other one is adapted to allow for the transdermal administration of therapeutically effective amounts of rotigotine for at least 4 days. In a preferred embodiment, the two transdermal therapeutic systems of the kit have the same rotigotine content and each of them is adapted to allow for the transdermal administration of therapeutically effective amounts of rotigotine for at least 4 days.

In a third aspect, the present invention provides a method for the preparation of the transdermal therapeutic system of the present invention.

In present invention the preparation method involves the use of a solvent system consisting of an aprotic polar solvent and a protic polar solvent.

In one embodiment, the preparation method involves the use of a solvent system consisting of an aprotic polar solvent and a protic polar solvent in a ratio of 2:1 to 9:1.

In a preferred embodiment, the solvent system consists of a carboxylic acid ester and an aliphatic alcohol. In a more preferred embodiment the solvent system consists of ethyl acetate and ethanol. In a particular preferred embodiment the solvent system consists of ethyl acetate and ethanol in a ratio of 2:1 to 6:1.

In a further embodiment, the preparation method involves the use of a solvent system consisting of heptane and ethanol in a ratio of 1.5:1 to 1:1.5.

In another preferred embodiment, the preparation method is carried out at room temperature and rotigotine is added to the solvent system in two portions. When rotigotine is added in two portions, one portion is added before and the other portion is added after polyvinylpyrrolidone is added.

In another preferred embodiment, the preparation method is carried out at room temperature and the total amount of rotigotine is added to the solvent system in one portion together with polyvinylpyrrolidone.

In another preferred embodiment, polyvinylpyrrolidone is first dissolved in the solvent system and adhesive mixture and rotigotine is then added to this pre-solution at room temperature.

In a further preferred embodiment, rotigotine of polymorphic Form II is used as starting material in the preparation method of the present invention.

In a further aspect, the present invention provides a transdermal therapeutic system comprising rotigotine as active ingredient for use in the treatment of patients suffering from Parkinson's disease, Parkinson's plus syndrome, depression, fibromyalgia and the restless-legs syndrome and for use in the treatment or prevention of dopaminergic neuron loss or the treatment or prevention of cognitive disorders by transdermal administration of rotigotine once or twice weekly, wherein the transdermal therapeutic system comprises a backing layer, a solvent-based rotigotine containing self-adhesive matrix layer as well as a release liner and is adapted to allow for the transdermal administration of therapeutically effective amounts of rotigotine for at least 3 days.

In one embodiment, the transdermal therapeutic system for the above use is administered once weekly and is adapted to allow for the transdermal administration of therapeutically effective amounts of rotigotine for at least 7 days.

In a further embodiment, the transdermal therapeutic system for the above use is administered twice weekly and the two transdermal therapeutic systems which are administered per week have the same or a different rotigotine content and are adapted to together allow for the transdermal administration of therapeutically effective amounts of rotigotine for at least 7 days.

In one embodiment, the two transdermal therapeutic systems for the above use which are administered per week have the same rotigotine content.

In another embodiment, two transdermal therapeutic systems for the above use which are administered per week have a different rotigotine content and one of them is adapted to allow for the transdermal administration of therapeutically effective amounts of rotigotine for at least 3 days and the other one is adapted to allow for the transdermal administration of therapeutically effective amounts of rotigotine for at least 4 days.

In a further embodiment, the self-adhesive matrix layer of the transdermal therapeutic system for the above use has a coating weight of about 75-400 $g/m^2$ and comprises a reservoir layer containing about 9-25 wt.-% rotigotine based on the weight of the reservoir layer.

In a another embodiment, the self-adhesive matrix layer of the transdermal therapeutic system for the above use has a coating weight of about 100-400 $g/m^2$ and comprises a reservoir layer containing about 9-20 wt.-% rotigotine based on the weight of the reservoir layer.

In a further embodiment, the self-adhesive matrix layer of the transdermal therapeutic system for the above use further comprises a skin adhesive layer containing rotigotine in a concentration of about 0-10 wt.-% based on the weight of the skin adhesive layer and the skin adhesive layer is provided between the reservoir layer and the release liner and has a lower rotigotine concentration than the reservoir layer.

In a preferred embodiment, the skin adhesive layer of the transdermal therapeutic system for the above use has a coating weight, which is no more than the coating weight of the reservoir layer.

In a further embodiment, the transdermal therapeutic system for the above use contains about 10-32 mg rotigotine/10 $cm^2$ surface of the self-adhesive matrix layer, preferably about 27 mg rotigotine/10 $cm^2$ surface of the self-adhesive matrix layer.

In a preferred embodiment, the reservoir layer or the reservoir layer and the skin adhesive layer, if it contains rotigotine, of the transdermal therapeutic system for the above use further contain(s) poly (N-vinyl-2-pyrrolidone) abbreviated here as polyvinylpyrrolidone or PVP and the rotigotine to polyvinylpyrrolidone weight ratio in the respective layer is 9:2 to 9:5, preferably 9:3 to 9:5, or multiples thereof.

In a further preferred embodiment, the reservoir layer and, if present, the skin adhesive layer of the transdermal therapeutic system for the above use each contain at least one, preferably two, amine-resistant silicone pressure sensitive adhesive(s).

DETAILED DESCRIPTION

The present invention provides in a first aspect a transdermal therapeutic system, comprising
(a) a backing layer,
(b) a solvent-based self-adhesive matrix layer containing rotigotine as active ingredient, and
(c) a release liner,
wherein the self-adhesive matrix layer has a coating weight of about 75-400 g/m$^2$ and comprises a reservoir layer containing about 9-25 wt.-% rotigotine based on the weight of the reservoir layer.

In a further embodiment of present invention the transdermal therapeutic system, comprises
(a) a backing layer,
(b) a solvent-based self-adhesive matrix layer containing rotigotine as active ingredient, and
(c) a release liner,
wherein the self-adhesive matrix layer has a coating weight of about 100-400 g/m$^2$ and comprises a reservoir layer containing about 9-20 wt.-% rotigotine based on the weight of the reservoir layer.

The term "transdermal therapeutic system" (TTS) as used herein refers to a matrix-type patch having a continuous self-adhesive matrix layer in its centre portion. Such a patch consists of a backing layer, the self-adhesive matrix layer and a release liner, which is removed before use. In the present application, the terms "transdermal therapeutic system", "TTS" and "patch" are equivalently used in order to describe the transdermal therapeutic system of the present invention.

The term "solvent-based" as used herein to describe the self-adhesive matrix layer of the transdermal therapeutic system of the present invention means that during the manufacturing process of the transdermal therapeutic system of the present invention rotigotine and the other components of the self-adhesive matrix layer are dissolved or dispersed and mixed in an organic solvent.

Figure 10:
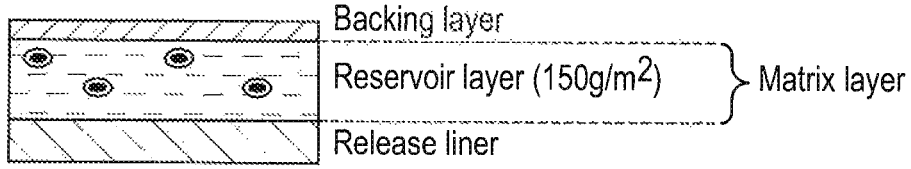
FIG. 10 shows schematic drawings of possible multi-day patch variants
Figure 10:
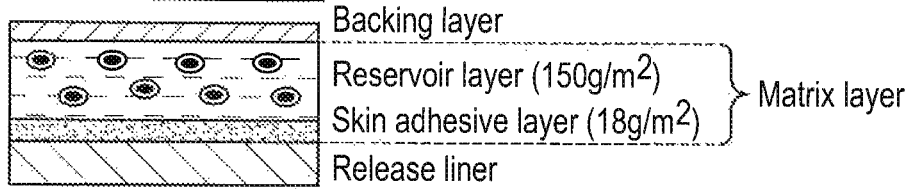
Figure 10:
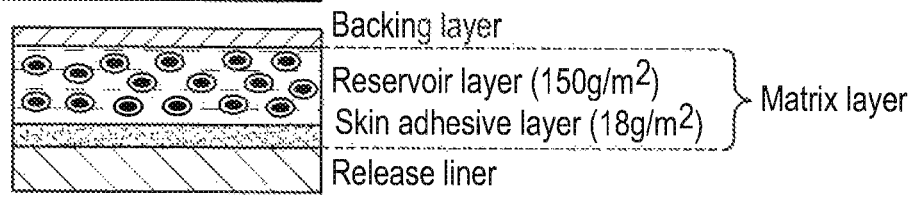
Figure 10:
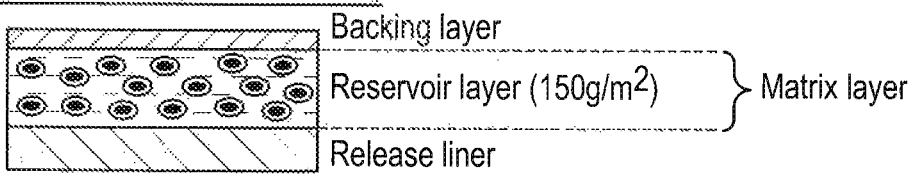
Figure 10:
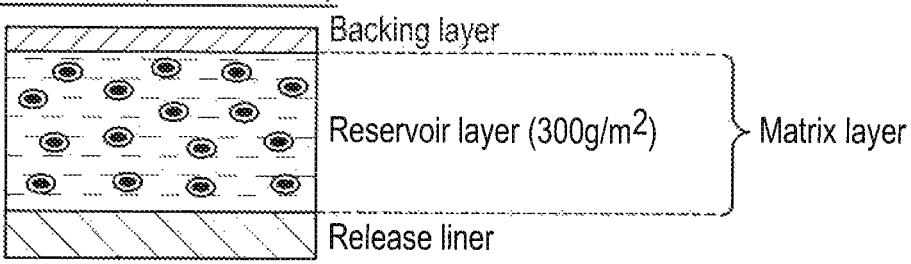
Figure 10:
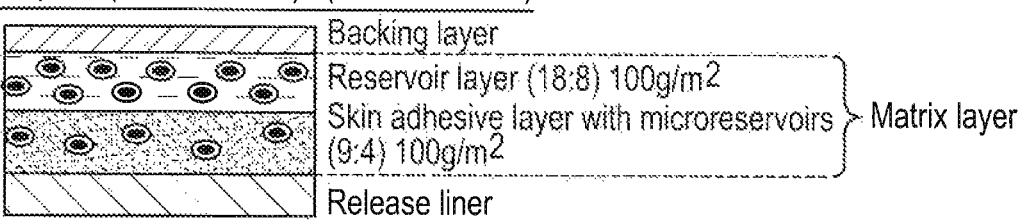

The term "self-adhesive matrix layer" as used herein describes the sum of adhesive containing layers, e.g. reservoir layer, skin adhesive layer and rotigotine containing skin adhesive layer and all combinations thereof as shown in FIG. 10. In case the transdermal therapeutic system contains only one reservoir layer, this reservoir layer represents the self-adhesive matrix layer.

The term "release liner" is used synonymous with protective foil or sheet.

This is in contrast to hot-melt manufacturing processes during which the components of a self-adhesive matrix layer of a transdermal therapeutic system are mixed in the absence of any solvent(s) in a heat molten state. Adhesives being suitable for use in a hot-melt manufacturing process exhibit a dynamic viscosity of no more than 60 Pa·s, no more than 80 Pa·s, no more than 100 Pa·s, no more than 120 Pa·s or at most 150 Pa·s at a temperature of 160° C. Depending on the dynamic viscosity of the employed adhesive(s) at 160° C., the addition of a softener, such as waxes, silicone oils, glycerin, condensates from glycerin with fatty acids or polyols, or laurylacetate, or, in particular, glycerolmonolaurate, laurylacetate, waxes of the formula R—C(O)—OR', alkylmethylsiloxane waxes, siloxated polyether waxes, organic waxes or glycerin, may be required to adjust the viscosity of the adhesive(s), in particular of silicone adhesive(s), in a suitable manner during hot-melt manufacturing processes.

Silicone adhesives being suitable for preparing the solvent-based self-adhesive matrix layer of the transdermal therapeutic system of the present invention without any additive(s) exhibit a dynamic viscosity of above 150 Pa·s at a temperature of 160° C. and therefore require the addition of a softener in order to be suitable for a hot-melt manufacturing process.

In one embodiment, the solvent-based self-adhesive matrix layer of the transdermal therapeutic system of the present invention does therefore not contain an adhesive having a dynamic viscosity of no more than 60 Pa·s, no more than 80 Pa·s, no more than 100 Pa·s, no more than 120 Pa·s or at most 150 Pa·s at a temperature of 160° C.

In another embodiment, the adhesive(s) used for preparing the solvent-based self-adhesive matrix layer of the transdermal therapeutic system of the present invention does/do not contain a softener, which after the addition to an adhesive lowers the viscosity of said adhesive to no more than 60 Pa·s, no more than 80 Pa·s, no more than 100 Pa·s, no more than 120 Pa·s or at most 150 Pa·s at a temperature of 160° C. Said softener may be selected from the group consisting of waxes, silicone oils, glycerin, condensates from glycerin with fatty acids or polyols, and laurylacetate or which may in particular be selected from the group consisting of glycerolmonolaurate, laurylacetate, waxes of the formula R—C(O)—OR', alkylmethylsiloxane waxes, siloxated polyether waxes, organic waxes and glycerin.

The transdermal therapeutic system of the present invention comprising a solvent-based self-adhesive matrix layer and a transdermal therapeutic system obtained by a hot-melt manufacturing process are characterized by different physicochemical properties, such as different drug release properties, even if the qualitative and quantitative composition of the respective transdermal therapeutic systems is identical.

The addition of one or more softeners to an adhesive will lower the dynamic viscosity of the adhesive in the heat molten state, but will at the same time also lower the cohesion of the self-adhesive matrix layer of an accordingly prepared final TTS thereby causing a loss of structural integrity due to an increased cold flow of the adhesive layer. This constraint is avoided by the solvent-based manufacturing process leading to the transdermal therapeutic system of the present invention.

The backing layer of the transdermal therapeutic system of the present invention is inert to the components of the self-adhesive matrix layer. It is a film being impermeable to rotigotine. Such a film may consist of polyester, polyamide, polyethylene, polypropylene, polyurethane, polyvinyl chloride or a combination of the aforementioned materials. These films may or may not be coated, e.g. with an aluminum film or with aluminum vapour or with a silicone layer. The thickness of the backing layer may be between 10 and 100 μm, preferably between 15 and 40 μm.

In one embodiment, the self-adhesive matrix layer is formed by a solid dispersion consisting of a dispersing agent and a dispersed phase, which is immiscible with the dispersing agent.

The dispersing agent of the solid dispersion may be any solid or semi-solid semi-permeable polymer or copolymer. The dispersing agent should provide sufficient activity and stability for the solid dispersion as well as sufficient release of rotigotine. Usually this polymer will be a pressure sensitive adhesive (PSA) or a mixture of such adhesives.

The solid dispersion forming the self-adhesive matrix layer of the transdermal therapeutic system of the present invention comprises an adhesive or a mixture of adhesives as dispersing agent and rotigotine as well as polyvinylpyrrolidone in the dispersed phase.

In a preferred embodiment, the self-adhesive matrix layer of the transdermal therapeutic system of the present invention contains about 10-32 mg rotigotine/10 cm² surface of the self-adhesive matrix layer, preferably about 13.5 mg or about 27 mg rotigotine/10 cm² surface of the self-adhesive matrix layer.

Preferably, the self-adhesive matrix layer of the transdermal therapeutic system of the present invention contains about 6-25 wt.-%, more preferred about 9-25 wt.-%, even more preferred about 9-20 wt.-% and most preferred about 9 or about 18 wt.-% rotigotine based on the weight of the self-adhesive matrix layer In one embodiment, the self-adhesive matrix layer comprises a reservoir layer. The reservoir layer represents a matrix layer and is formed by a solid dispersion in terms of the foregoing. In a preferred embodiment, the self-adhesive matrix layer only comprises one reservoir layer and does not contain any additional matrix layer, i.e., in a preferred embodiment, the self-adhesive matrix layer represents a "mono-layer" matrix.

In another embodiment, the self-adhesive matrix layer may contain more than one reservoir layer, for example 2, 3, 4 or 5 reservoir layers.

The reservoir layer contains about 9-25 wt.-%, preferably about 9-20 wt.-% and most preferably about 9 wt.-% or about 18 wt.-% rotigotine based on the weight of the reservoir layer.

The reservoir layer has a coating weight of about 75-400 g/m², preferably about 100-400 g/m², more preferably about 75-300 g/m², more preferably about 75-200 g/m², even more preferably 100-150 g/m² and most preferably about 150 g/m².

In a further embodiment, the reservoir layer of the transdermal therapeutic system has a coating weight of about 75-300 g/m², preferably about 75-200 g/m², more preferably about 100-150 g/m² and most preferably about 150 g/m² and contains about 9-25 wt.-% rotigotine, preferably about 9-20 wt.-% rotigotine, more preferably about 9 wt.-% or about 18 wt.-% rotigotine based on the weight of the reservoir layer.

In a another embodiment, the reservoir layer of the transdermal therapeutic system has a coating weight of about 75-300 g/m², preferably of about 75-200 g/m², more preferably about 100-150 g/m² and most preferably about 150 g/m² and contains about 9-25 wt.-% rotigotine, preferably about 9-20 wt.-% rotigotine, more preferably about 9 wt.-% or about 18 wt.-% rotigotine based on the weight of the reservoir layer and a skin adhesive layer that has a coating weight of about 10-150 g/m².

In a further embodiment, the self-adhesive matrix layer further comprises a skin adhesive layer. Similar to the reservoir layer, the skin adhesive layer represents a matrix layer and is preferably formed by a solid dispersion in terms of the foregoing. The skin adhesive layer is provided between the reservoir layer and the release liner. In one embodiment, the skin adhesive layer contains no active ingredient, i.e. no rotigotine. In another embodiment, the skin adhesive layer contains rotigotine.

In a preferred embodiment, the self-adhesive matrix layer comprises a reservoir layer and a skin adhesive layer and does not contain any additional matrix layer, i.e., in a preferred embodiment, the self-adhesive matrix layer represents a "bi-layer" matrix.

The skin adhesive layer avoids a direct skin contact of the reservoir layer, which contains in some embodiments a high concentration of rotigotine, which would potentially cause local skin irritation, or might show diminished skin adhesiveness due to the high drug load. The skin adhesive layer therefore contains either no rotigotine or, if it contains rotigotine, has a lower rotigotine concentration than the reservoir layer, if the rotigotine concentration of the latter exceeds 9 wt.-%. For example, results obtained for the daily application of a TTS having a self-adhesive matrix layer only comprising a reservoir layer, i.e. a "mono-layer" matrix, containing 9 wt.-% rotigotine and 4 wt.-% PVP, have shown a good skin tolerability. The composition of the respective reservoir layer thus also represents a reasonable composition for a skin adhesive layer of a self-adhesive bi-layer matrix of the transdermal therapeutic system of the present invention. In a preferred embodiment, the self-adhesive matrix layer therefore is built up of one or more reservoir layer(s) and a skin adhesive layer, wherein the rotigotine/PVP concentration is increasing from the skin towards the backing layer in order to provide for sufficient skin tolerability, sufficient tack of the skin adhesive layer and a high drug concentration in the reservoir layer. Moreover, adequately adjusting the rotigotine/PVP content in the reservoir layer(s) and the skin adhesive layer allows for modifying the onset of drug release and the release profile of the transdermal therapeutic system of the present invention in vivo.

The skin adhesive layer contains rotigotine in a concentration of about 0-10 wt.-%, preferably about 0-9 wt.-% and most preferably about 6-9 wt.-% based on the weight of the skin adhesive layer, and has a lower rotigotine concentration than the reservoir layer.

Due to the lower rotigotine concentration in the skin adhesive layer, the transdermal therapeutic system of the present invention comprising a reservoir layer and a skin adhesive layer represents a gradient system being characterized by an increase of the rotigotine concentration from the surface of the skin adhesive layer being in contact with the patient's skin upon administration towards the reservoir layer and the backing layer.

The skin adhesive layer has a coating weight of about 10-150 g/m², preferably about 15-120 g/m², such as e.g. about 15-50 g/m² or about 50-100 g/m².

In a preferred embodiment, the coating weight of the skin adhesive layer is no more than the coating weight of the reservoir layer.

In a further preferred embodiment, the reservoir layer has a coating weight of about 75-200 g/m², preferably 100-150 g/m², and more preferably 150 g/m² and contains about 18 wt.-% rotigotine based on the weight of the reservoir layer.

In another preferred embodiment, the reservoir layer has a coating weight of about 75-200 g/m², preferably 100-150 g/m², and more preferably 150 g/m² and contains about 18 wt.-% rotigotine based on the weight of the reservoir layer and the skin adhesive layer has a coating weight of about 10-150 g/m².

In another preferred embodiment, the reservoir layer and the skin adhesive layer have the same coating weight. For example, the reservoir layer and the skin adhesive layer may each have a coating weight of 100 g/m² or 150 g/m².

In another preferred embodiment, the skin adhesive layer has a coating weight of about 15-120 g/m² and contains about 5-10 wt.-% rotigotine based on the weight of the skin adhesive layer.

In another preferred embodiment, the skin adhesive layer has a coating weight of about 15-50 g/m² and contains about 0-5 wt.-% rotigotine based on the weight of the skin adhesive layer.

The term "coating weight" as used herein in connection with the skin adhesive layer or reservoir layer or self-adhesive matrix layer refers to the mass per area unit of each individual layer or the sum of individual layers after removal of the solvent, except backing layer and release liner. In this connection coating weight is synonymous with area weight.

The following table 1A shows particular preferred embodiments of the self-adhesive matrix layer of the transdermal therapeutic system of the present invention.

TABLE 1A

Composition of preferred embodiments of the self-adhesive matrix layer of the transdermal therapeutic system of the present invention

| Ingredient [mg/10 cm$^2$], except stated otherwise | | Embodiment (corresp. Example) | | | | | |
|---|---|---|---|---|---|---|---|
| | | 1 (1) | 2 (2) | 3 (3) | 4 (4, 8, 9) | 5 (5, 6) | 6 (7) |
| Reservoir layer | Rotigotine | 13.5 | 27.0 | 27.0 | 27.0 | 27.0 | 18.0 |
| | Rotigotine content [wt.-%] | 9.0 | 18.0 | 18.0 | 18.0 | 9.0 | 18.0 |
| | PVP | 3.0 | 6.0 | 12.0 | 12.0 | 12.0 | 8.0 |
| | PVP content [wt.-%] | 2.0 | 4.0 | 8.0 | 8.0 | 4.0 | 8.0 |
| | Rotigotine:PVP | 9:2 | 9:2 | 9:4 | 9:4 | 9:4 | 9:4 |
| | Coating weight [g/m$^2$] | 150.0 | 150.0 | 150.0 | 150.0 | 300.0 | 100.0 |
| Skin adhesive layer | Rotigotine | — | — | — | — | — | 9.0 |
| | Rotigotine content [wt.-%] | — | — | — | — | — | 9.0 |
| | PVP | — | — | — | — | — | 4.0 |
| | PVP content [wt.-%] | — | — | — | — | — | 4.0 |
| | Rotigotine:PVP | — | — | — | — | — | 9:4 |
| | Coating weight [g/m$^2$] | — | 18.0 | 18.0 | — | — | 100.0 |

A TTS having a self-adhesive matrix layer according to embodiment 1 of the above table allows for the transdermal administration of therapeutically effective amounts of rotigotine for at least 4 days, i.e. it represents a 4-day patch.

A TTS having a self-adhesive matrix layer according to any of embodiments 2, 3, 4, 5 or 6 of the above table allows for the transdermal administration of therapeutically effective amounts of rotigotine for at least 7 days, i.e. it represents a 7-day patch.

The term "at least" as used herein in connection with the respective number of days to describe the duration of the transdermal administration of therapeutically effective amounts of rotigotine means that rotigotine is administered for the respective number of days or more. For example, "at least 7 days" means that therapeutically effective amounts of rotigotine are administered for 7 days or more.

The term "administration of therapeutically effective amounts of rotigotine" as used herein refers to the adjustment rotigotine plasma concentrations in a patient suffering from a disease to be treated with rotigotine, which lie within the therapeutic window of rotigotine for the treatment of the respective disease. For example, by administering a therapeutically effective amount of rotigotine in the treatment of Parkinson's disease, a rotigotine plasma concentration of between about 0.2 and 1.2 ng/ml during maintenance phase is adjusted and by administering a therapeutically effective amount of rotigotine in the treatment of RLS, a rotigotine plasma concentration of between about 0.1 and 0.5 ng/ml during maintenance phase is adjusted.

The commercial rotigotine-containing Neupro® patches of the applicant allow for the transdermal administration of therapeutically effective amounts of rotigotine for 1 day and contain 4.5 mg/10 cm$^2$ rotigotine. Based on this content, a theoretical amount of rotigotine of 18.0 mg being required for a 4-day patch and of 31.5 mg for a 7-day patch can be calculated.

However, it was surprisingly found that a rotigotine amount of about 13.5 mg in a TTS of the present invention was sufficient to allow for the transdermal administration of therapeutically effective amounts of rotigotine for 4 days and that a rotigotine amount of about 27.0 mg in a TTS of the present invention was sufficient to allow for the transdermal administration of therapeutically effective amounts of rotigotine for 7 days.

Table 1B gives an overview on the combination of modifying the coating weight of the reservoir layer and the rotigotine content within the reservoir layer in wt.-% to obtain the therapeutically effective amounts of rotigotine for application periods between 1 and 7 days.

TABLE 1B

Content of rotigotine in reservoir layer depending on the coating weight to achieve the therapeutically effective amounts for the targeted application period
Content of rotigotine in reservoir layer [wt.-%]

| Application period [days] | API content [mg/ 10 cm$^2$] | Coating weight of reservoir [g/m$^2$] | | | | | | |
|---|---|---|---|---|---|---|---|---|
| | | 50 | 75 | 100 | 150 | 200 | 250 | 300 |
| 1*[1] | 4.50 | 9.00 | 6.00 | 4.50 | 3.00 | 2.25 | 1.80 | 1.50 |
| 3*[1] | 13.5 | 27.00 | 18.00 | 9.00 | 9.00 | 6.75 | 5.40 | 4.50 |
| 3.5*[1] | 15.75 | 31.50 | 21.00 | 13.50 | 10.50 | 7.88 | 6.30 | 5.25 |
| 4*[1] | 18.00 | 36.00 | 24.00 | 15.75 | 12.00 | 9.00 | 7.20 | 6.00 |
| 7*[1] | 31.50 | 63.00 | 42.00 | 18.00 | 21.00 | 15.75 | 12.60 | 10.50 |
| 3*[2] | 11.57 | 23.14 | 15.43 | 31.50 | 7.71 | 5.79 | 4.63 | 3.86 |
| 3.5*[2] | 13.50 | 27.00 | 18.00 | 11.57 | 9.00 | 6.75 | 5.40 | 4.50 |
| 4*[2] | 15.43 | 30.86 | 20.57 | 13.50 | 10.29 | 7.71 | 6.17 | 5.14 |
| 7*[2] | 27.00 | 54.00 | 36.00 | 15.43 | 18.00 | 13.50 | 10.80 | 9.00 |

*[1]therapeutically effective amounts in TTS
*[2]reduced sufficient therapeutically effective amounts in TTS, e.g. 27 mg sufficient for 7 days In case of a gradient patch comprising a rotigotine containing skin adhesive layer according to FIG. 10 the required rotigotine amount in the reservoir layer can be reduced by the rotigotine amount in the skin adhesive layer to obtain required therapeutically effective amount.

That is, a sub-additive increase of the total rotigotine content in the transdermal therapeutic system of the present invention led to the targeted constant in vivo drug release profiles over application periods of at least 3 days and up to at least 7 days. This allows for the saving of about one daily dose of rotigotine, and associated cost of goods, for a twice weekly or once weekly administered patch according to the present invention compared to the daily administration of the patches known from the prior art.

The adhesives used in the present invention should preferably be pharmaceutically acceptable in a sense that they are biocompatible, non-sensitising and non-irritating to the skin of the patient. Particularly advantageous adhesives for use in the present invention should further meet the following requirements:
1. Retained adhesive and co-adhesive properties in the presence of moisture or perspiration under normal temperature variations, and
2. Good compatibility with rotigotine, as well as with the further excipients.

Although different types of pressure sensitive adhesives may be used in the present invention, it is preferred to use lipophilic adhesives having both low drug and low water absorption capacity. Preferably, the adhesives have solubility parameters which are lower than those of rotigotine. Such preferred pressure sensitive adhesives are amine-resistant silicone pressure sensitive adhesives.

The term "amine-resistant" as used herein means that the respective adhesives being characterized as amine-resistant adhesives do not react in any way with the tertiary amino-group of rotigotine.

In one embodiment the dispersing agent comprises at least one silicone pressure sensitive adhesive and preferably a mixture of at least one high tack and at least one medium tack silicone pressure sensitive adhesive.

In a preferred embodiment, the reservoir layer and, if present, the skin adhesive layer of the transdermal therapeutic system of the present invention each contain at least one, preferably two, amine-resistant silicone pressure sensitive adhesive(s) and most preferably, a mixture of at least one high tack and at least one medium tack silicone pressure sensitive adhesive.

Especially preferred pressure sensitive silicone adhesives are of the type forming a soluble polycondensed polydimethylsiloxane (PDMS)/resin network, wherein the hydroxy groups are capped with e.g. trimethylsilyl (TMS) groups. Preferred adhesives of this kind are the BIO-PSA silicone pressure sensitive adhesives manufactured by Dow Corning, particularly the 7-4201 and 7-4301 qualities as well as the 7-4202 and 7-4302 qualities.

In another embodiment, blends or copolymers of the above silicone adhesives with other silicone adhesives or further pressure sensitive adhesives selected from the group consisting of a styrenic polymer, a polyisobutylene, or mixtures thereof as well as an acrylate-based non-aqueous polymer adhesive may be used for preparing the reservoir layer and, if present, the skin adhesive layer of the transdermal therapeutic system of the present invention. Suitable styrenic polymers are for example styrenic triblock copolymers such as styrene-ethylene-styrene (SES), styrene-butadiene-styrene (SBS), styrene-isoprene-styrene (SIS), styrene-ethylene/butylene-styrene (S-EB-S), styrene-ethylene/butylene/propylene-styrene (S-EBP-S), styrene-isoprene/butadiene-styrene (S-IB-S), or mixtures thereof, optionally in combination with a styrenic diblock copolymer such as styrene-ethylene (SE), styrene-butadiene (SB), styrene-isoprene (SI), styrene-ethylene/butadiene-styrene (SE-BS), styrene-ethylene/propylene (S-EP), or mixtures thereof. A suitable acrylate-based polymer adhesive preferably contains at least two of the following monomers: acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate or vinylpyrrolidone.

In a preferred embodiment, the reservoir layer and the skin adhesive layer are both based on the same adhesive(s). For example, the reservoir layer and the skin adhesive layer may both contain one or more amine-resistant silicone pressure sensitive adhesive(s). Likewise, if any of the above blends or copolymers is used as adhesive in the reservoir layer, the skin adhesive layer would preferably also be based on this blend or copolymer.

Tack has been defined as the property that enables an adhesive to form a bond with the surface of another material upon brief contact under light pressure (see e.g. "Pressure Sensitive Tack of Adhesives Using an Inverted Probe Machine", ASTM D2979-71 (1982); H. F. Hammond in D. Satas "Handbook of Pressure Sensitive Adhesive Technology" (1989), $2^{nd}$ ed., Chapter 4, Van Nostrand Reinhold, New York, page 38).

Medium tack of a silicone pressure sensitive adhesive indicates that the immediate bond to the surface of another material is weaker compared to a high tack silicone adhesive.

Specific tack values of silicone pressure sensitive adhesives for use in the present invention can for example be determined by the Corporate Test Method (CTM) 0991 of Dow Corning.

The resin/polymer ratio of the especially preferred pressure sensitive silicone adhesives for use in the present invention is 59-61/41-39 for medium tack adhesives, whereas it is 54-56/46-44 for high tack adhesives. It is known to the skilled person that both tape and rheological properties are significantly influenced by the resin/polymer ratio (K. L. Ulman and R. P. Sweet "The Correlation of Tape Properties and Rheology" (1998), Information Brochure, Dow Corning Corp., USA).

Blends comprising a high tack and a medium tack silicone type pressure sensitive adhesive comprising polysiloxane with a resin are advantageous in that they provide for the optimum balance between good adhesion and little cold flow. Excessive cold flow based on too soft solid dispersions is disadvantageous since it may lead to a loss of the structural integrity of the self-adhesive matrix layer of a TTS at the application site and as a consequence to silicone residues sticking on the patient's skin or clothes.

Preferably, the weight ratio of a high tack to a medium tack silicone pressure sensitive adhesive in these blends is about 1:1. However, this does not exclude employing any other weight ratio.

A mixture of the aforementioned 7-4201/7-4202 (medium tack) and 7-4301/7-4302 (high tack) qualities proved to be especially useful for the preparation of the self-adhesive matrix layer of the transdermal therapeutic system of the present invention. In such a mixture, the overall resin/polymer ratio preferably is 56-58/44-42.

For the preparation of the self-adhesive matrix layer of the transdermal therapeutic system of the present invention, the employed silicone adhesives are dissolved in an organic solvent. The transdermal therapeutic system of the present invention therefore represents a solvent-based transdermal therapeutic system as it was defined in the foregoing and is different from transdermal therapeutic systems obtained by a hot melt process. During preparation of the self-adhesive matrix layer, the organic solvent is finally evaporated.

Suitable organic solvents for use in the preparation of the transdermal therapeutic system of the present invention are alkanes, carboxylic acid ester, alcohols and ketones, for example, heptane, ethyl acetate, ethanol and acetone, as well as mixtures thereof.

In a preferred embodiment, a mixture of heptane and ethanol is used as organic solvent, and in a particularly preferred embodiment, a mixture of ethyl acetate and ethanol is used as organic solvent.

The solid or semi-solid semi-permeable polymer representing the dispersing agent of the solid dispersion forming the self-adhesive matrix layer has to satisfy the following requirements:
 1. Sufficient solubility and permeability for the free base form of rotigotine.
 2. Impermeability for the protonated form of rotigotine.

In one embodiment the solubility of rotigotine (without stabilizer) in the dispersing agent is about 5 wt.-% or below and in another embodiment about 3 wt.-% or below. In still another embodiment the solubility of rotigotine (without stabilizer) in the dispersing agent is about 2 wt.-% or below and in another embodiment it is about 0.1 wt.-% or below.

The dispersed phase of the solid dispersion comprises rotigotine in non-crystalline form and a stabilizer, for example polyvinylpyrrolidone, and optionally further pharmaceutically acceptable excipients, such as permeation enhancers and antioxidants.

Polyvinylpyrrolidone is able to stabilize solid dispersions of the non-crystalline form of rotigotine by preventing rotigotine from crystallization. In one embodiment the stabilizer is selected from polyvinylpyrrolidone and in a preferred embodiment from water soluble polyvinylpyrrolidone. Copolymers of polyvinylpyrrolidone and vinyl acetate, polyethyleneglycol, polypropyleneglycol, glycerol and fatty acid esters or copolymers of ethylene and vinylacetate might also be considered for such use.

Polyvinylpyrrolidone (PVP) is a polymer made from the monomer N-vinylpyrrolidone. It increases the cohesion of silicone adhesives. The molecular weight of polyvinylpyrrolidone can be in the range from 2,000 to 2,500,000 Dalton (g/mol) (given as weight average), in one embodiment in the range from 700 000 to 1,500,000, in another embodiment in the range from 1,000,000 to 1,500,000 Dalton. Various grades of PVP are commercially available from e.g. BASF Aktiengesellchaft of Ludwigshafen, Germany, e.g. under the name of Kollidon. For example, the following grades of Kollidons are water soluble forms of PVP: K-12 PF (molecular weight=2,000-3,000); K-17 PF (molecular weight=7,000-11,000); K-25 (molecular weight=28,000-34,000); K-30 (molecular weight=44,000-54,000); and K-90 F (molecular weight=1,000,000-1,500,000). In a preferred embodiment, the molecular weight of polyvinylpyrrolidone is in the range from 28,000 to 1,500,000 Dalton (g/mol). Particularly preferred are the Kollidon grades K-25, K-30 and K-90F.

The rotigotine to polyvinylpyrrolidone weight ratio in the dispersed phase is 9:2 to 9:5, preferably 9:3 to 9:5, and particularly preferred 9:4, or multiples thereof. The term "multiples thereof" as used in this context means that based on a weight ratio of rotigotine to polyvinylpyrrolidone of for example 9:4, also a weight ratio of 18:8 or 27:12, etc. is encompassed.

In a preferred embodiment, the self-adhesive matrix layer of the transdermal therapeutic system of the present invention comprises a reservoir layer and the reservoir layer contains rotigotine and polyvinylpyrrolidone and the rotigotine to polyvinylpyrrolidone weight ratio in the reservoir layer is 9:2 to 9:5, preferably 9:3 to 9:5, and particularly preferred 9:4, or multiples thereof.

In another preferred embodiment, the self-adhesive matrix layer of the transdermal therapeutic system of the present invention comprises a reservoir layer and a skin adhesive layer and the reservoir layer and the skin adhesive layer, if it contains rotigotine, further contain polyvinylpyrrolidone and the rotigotine to polyvinylpyrrolidone weight ratio in the respective layer is 9:2 to 9:5, preferably 9:3 to 9:5, and particularly preferred 9:4, or multiples thereof.

A decrease of the rotigotine to polyvinylpyrrolidone weight ratio from 9:2 to 9:4 has shown to provide for good physical stability of the corresponding single-day transdermal therapeutic systems (see WO 2011/076879). An equivalent stabilizing effect could also be shown for the multi-day transdermal therapeutic system of the present invention having a higher rotigotine/PVP load per $cm^2$.

Suitable permeation enhancers may be selected from the group of fatty alcohols, fatty acids, fatty acid esters, fatty acid amides, glycerol or its fatty acid esters, N-methylpyrrolidone, terpenes such as limonene, [alpha]-pinene, [alpha]-terpineol, carvone, carveol, limonene oxide, pinene oxide, 1,8-eucalyptol and most preferably ascorbyl palmitate. In a preferred embodiment, the TTS of the present disclosure does not contain a penetration enhancer.

Suitable antioxidants are sodium metabisulfite, ascorbyl palmitate and DL-alpha tocopherol.

In one embodiment of the invention the water content of the solid dispersion is less than 1.0 wt.-% and in another embodiment it is less than 0.5 wt.-% related to the total weight of the self-adhesive matrix layer. In one embodiment, the self-adhesive matrix layer is substantially free of water, i.e. no water is used during the manufacturing process or the water is removed during the manufacturing process as complete as possible.

In a particular preferred embodiment, the self-adhesive matrix is free of particles, which can absorb salts of rotigotine on the TTS/skin interface. Examples of particles, which can absorb salts of rotigotine on the TTS/skin interface, include silica. Such particles, which can adsorb salts of rotigotine, may represent diffusion barriers for the free base form of the drug and may result in the formation of channels inducing some permeability of the self-adhesive matrix for the protonated form of rotigotine, which is disadvantageous.

Preferably, the TTS contains less than 1 wt.-% of inorganic silicates, most preferably it is completely free from inorganic silicates.

The release liner will be removed immediately prior to use, i.e. immediately before the TTS will be brought into contact with the patient's skin. The release line may consist of polyester, polyethylene or polypropylene, which may or may not be coated, e.g. with aluminum film or aluminum vapour or fluoropolymers or with a silicone layer. Typically, the thickness of such a release liner ranges between 50 and 150 μm.

So as to facilitate removal of the release liner when wishing to apply the TTS, the release liner may comprise separate release liner having overlapping edges, similar to the kind used with the majority of conventional plasters.

In one embodiment, the transdermal therapeutic system of the present invention has a basal surface area of 5-50 $cm^2$, preferably 5-40 $cm^2$ such as for example 5 $cm^2$, 10 $cm^2$, 15 $cm^2$, 20 $cm^2$, 30 $cm^2$ or 40 $cm^2$. The term "basal surface area" as used herein refers to the surface of the self-adhesive matrix layer being in contact with the patient's skin upon administration.

Any references to rotigotine in the context of this invention and the claims of this application mean rotigotine in the form of its free base. In some cases, however, traces of rotigotine hydrochloride may be contained in a rotigotine preparation but these traces typically do not exceed 5 wt.-%, based on the amount of the free base. More preferably the content of hydrochloride impurities should be less than 2 wt.-%, even more preferably less than 1 wt.-% and most preferably the rotigotine used in the present invention contains less than 0.1 wt.-% or no hydrochloride impurities at all.

A further step, which may be taken for reducing the amount of the salt form of rotigotine, is isolating the free base form of rotigotine in solid form prior to the preparation of the solid dispersion. Alternatively, the free base of rotigotine may be produced in situ during the manufacture of the solid dispersion by neutralizing an acid addition salt of rotigotine.

It will be understood by a person skilled in the art that rotigotine exists in various stereoisomeric forms. It thus has also to be understood that besides the S-enantiomer, i.e. rotigotine, the R-enantiomer or a mixture of the different stereoisomers may be used in the present invention. Hence, the S- or R-enantiomer or the racemate or any other enantiomeric mixture of rotigotine may be used. Most preferred, the pure S-enantiomer, i.e. rotigotine, is used.

In the dispersed phase of the solid dispersion forming the self-adhesive matrix layer of the transdermal therapeutic system of the present invention, rotigotine is present in non-crystalline form.

In one embodiment the non-crystalline form of rotigotine is amorphous rotigotine.

The rotigotine starting material used for preparing the transdermal therapeutic system of the present invention exists in two different polymorphic states, polymorphic Form I and polymorphic Form II. Polymorphic Form II of rotigotine is described in WO 2009/068520 and has at least one of the following characteristics:

a X-ray powder diffraction spectrum comprising a peak at least at one of the following ° 2θ angles (±0.2): 12.04, 13.68, 17.72 and/or 19.01, measured with Cu—$K_\alpha$ irradiation (1.54060 Å);

a Raman spectrum comprising at least one peak at the following wave numbers (±3 cm$^{-1}$): 226.2, 297.0, 363.9, 737.3, 847.3, 1018.7 and/or 1354.3;

a differential scanning calorimetry (DSC) peak with a $T_{onset}$ at 97° C.±2° C. measured with a heating rate of 10° C./min; and/or a melting point of 97° C.±2° C.

In a preferred embodiment, rotigotine of polymorphic Form II is used as starting material for preparing the transdermal therapeutic system of the present invention.

While not wishing to be bound by theory it is believed that free rotigotine is molecularly dispersed in the dispersing agent of the solid dispersion forming the self-adhesive matrix layer of the transdermal therapeutic system of the present invention and that a non-crystalline form of rotigotine is reversibly associated with PVP by forming an inner phase or microreservoir.

In one embodiment the non-crystalline form of rotigotine is amorphous rotigotine. One advantage of a stable solid drug dispersion is that it can significantly reduce constraints often caused by low drug solubility in polymers suitable for transdermal delivery.

The term "microreservoirs" as used herein is meant to be understood as particulate, spatially and functionally separate compartments consisting of a mixture of rotigotine and polyvinylpyrrolidone, which are dispersed (as dispersed phase) in the dispersing agent of the solid dispersion as defined above. The term "microreservoirs" as used herein is further meant to be understood as amorphous micro-spheres dispersed in a polymer matrix and which can be differentiated from the surrounding outer phase by their high drug load in accordance to their reservoir function.

In one embodiment the solid dispersion contains 10$^3$ to 10$^9$ microreservoirs per cm$^2$ of its surface, in another embodiment 10$^6$ to 10$^9$ microreservoirs per cm$^2$ of its surface. This further illustrates the very small or "micro"-scopic appearance of microreservoirs of present invention.

The maximum diameter of the microreservoirs is less than the thickness of the solid dispersion, preferably up to 85% of the thickness of the solid dispersion, particularly preferred 5 to 74% of the thickness of the solid dispersion. For an exemplary thickness of the solid dispersion of 50 µm this corresponds to a maximum diameter of the microreservoirs in the range of preferably up to approximately 40 to 45 µm.

The term "maximum diameter" as used herein is meant to be understood as the diameter of the microreservoirs in that dimension (x-, y-, or z-dimension), which is the largest. It is clear for the skilled person that in case of spherical diameters the maximum diameter corresponds to the microreservoir's diameter. However, in the case of microreservoirs, which are not shaped in the form of spheres, i.e. of different geometric forms-, the x-, y- and z-dimensions may vary greatly.

In a particularly preferred embodiment of the invention, the mean diameter of the rotigotine containing microreservoirs distributed in the solid dispersion is in the range of 1 to 40%, even more preferred 1 to 20%, of the thickness of the solid dispersion. For an exemplary thickness of the solid dispersion of 50 µm this corresponds to a mean diameter of the microreservoirs in the range of preferably 0.5 to 20 µm.

The term "mean diameter" as used herein is defined as the mean value of the x, y, z-average diameters of all microreservoirs. The target particle size can be adjusted by the solid content and the viscosity of the solid dispersion.

The maximum and mean diameters of the microreservoirs as well as the number of microreservoirs per surface area of the solid dispersion can be determined as follows: The surface of the solid dispersion is examined with a light microscope (Leica microscope type DM/RBE equipped with a camera type DS Camera Head DS-5M). The measurement is performed by incidental polarized light analysis using a microscope at 200× magnification. A picture analysis is performed using the software Nikon LuciaG, Version 5.30, resulting in mean and maximum diameters for each sample.

In a preferred embodiment rotigotine and polyvinylpyrrolidone are contained in the transdermal therapeutic system of the present invention in a multitude of microreservoirs.

Due to the presence of rotigotine and polyvinylpyrrolidone in the self-adhesive matrix layer of the transdermal therapeutic system of the present invention in the form of distinct microreservoirs, the homogenous distribution of rotigotine within the self-adhesive matrix layer remains constant during storage. That is, the transdermal therapeutic system of the present invention is characterized by very good storage stability properties.

The transdermal therapeutic system of the present invention contains rotigotine as active ingredient. Rotigotine is a dopamine D1/D2/D3-receptor agonist and the transdermal therapeutic system of the present invention is therefore useful in the treatment of diseases susceptible to the action of dopamine receptor agonists.

In particular, the transdermal therapeutic system of the present invention can be used in the treatment of patients suffering from Parkinson's disease, Parkinson's plus syndrome, depression, fibromyalgia and the restless-legs syndrome. Furthermore, the transdermal therapeutic system of the present invention can be used in the treatment or prevention of dopaminergic neuron loss or cognitive disorders.

The use of solvent-based transdermal therapeutic systems containing rotigotine as active ingredient in the treatment of the above disease and in particular in the treatment of Parkinson's disease and in the treatment of the restless leg syndrome is known from the prior art. This treatment usually is a permanent treatment during which one single-day transdermal therapeutic system is administered every day. In particular, the permanent treatment involves the application of one or sometimes more transdermal therapeutic system(s) at a certain place of the patient's body, the removal of the respective patch(es) after one day of wearing and the application of one or more new patch(es) at another place of the patient's body.

In contrast, the multi-day solvent-based transdermal therapeutic system of the present invention is adapted to allow for the transdermal administration of therapeutically effective amounts of rotigotine for at least 3-7 days, including at least 3, at least 4, at least 5, at least 6 and at least 7 days. That is, by the transdermal therapeutic system of the present invention, the frequency of administration and the number of patches to be administered in the permanent treatment of the above diseases can be reduced, thereby providing for an improved treatment in that patient's comfort and compliance are enhanced. Moreover, due to the specific construction of the multi-day solvent-based transdermal therapeutic system of the present invention its skin tolerance is comparable to the skin tolerance of the single-day solvent-based transdermal therapeutic systems known from the prior art.

The transdermal administration of therapeutically effective amounts of rotigotine for at least 3-7 days by the transdermal therapeutic system of the present invention is achieved by choosing an appropriate composition of the self-adhesive matrix layer. As it was described above, this in particular includes appropriately adjusting the coating weight, the rotigotine content and the optional provision of a skin adhesive layer.

In a preferred embodiment, the transdermal therapeutic system of the present invention is adapted to allow for the transdermal administration of therapeutically effective amounts of rotigotine for at least 3, at least 4 or at least 7 days.

Most preferred, the transdermal therapeutic system of the present invention is adapted to allow for the transdermal administration of therapeutically effective amounts of rotigotine for at least 7 days.

Based on the respective composition, the multi-day solvent-based transdermal therapeutic system of the present invention can be applied in the following dosage regimens:

TABLE 2

Possible dosage regimens of the transdermal therapeutic system of the present invention

| Patch(es)* | Sequence of administration |
|---|---|
| 3-day patch | Every $3^{rd}$ day |
| 3.5-day patch | Twice weekly at two predetermined days, e.g. every $3^{rd}$ and $4^{th}$ day or every $4^{th}$ and $3^{rd}$ day |
| 4-day patch | Every $4^{th}$ day or twice weekly at two predetermined days, e.g. every $3^{rd}$ and $4^{th}$ day or every $4^{th}$ and $3^{rd}$ day |
| 5-day patch | Every $5^{th}$ day or once weekly at a predetermined day |
| 6-day patch | Every $6^{th}$ day or once weekly at a predetermined day |
| 7-day patch | Once weekly at a predetermined day, i.e. every $7^{th}$ day |
| One 3-day patch and one 4-day patch | Twice weekly at two predetermined days, e.g. every $3^{rd}$ and $4^{th}$ day or every $4^{th}$ and $3^{rd}$ day |

*The drug content of the patches allows for the transdermal administration of therapeutically effective amounts of rotigotine for 3, 3.5, 4, 5, 6 or 7 days. Based on their respective drug content, the patches are accordingly identified as 3-day patch, 3.5 day patch, 4-day patch, 5-day patch, 6-day patch or 7-day patch.

As discussed in the foregoing, the patches of the present invention are usually applied in a chronic treatment and should therefore preferably be administered at about the same time, e.g. at almost the same hour in the morning or in the evening. This in particular applies, when administering the patches of the present invention in accordance with one of the dosage regimens shown in Table 2.

In a particular preferred embodiment, one patch of the present invention allowing for the transdermal administration of therapeutically effective amounts of rotigotine for 7 days, i.e. a 7-day patch is administered per week at a predetermined day, corresponding to a once weekly administration of a transdermal therapeutic system of the present invention.

In another preferred embodiment, one 3-day patch and one 4-day patch, or two 3.5-day patches, or particularly preferred two 4-day patches are administered per week, corresponding to a twice weekly administration of a transdermal therapeutic system of the present invention. Independent of administering one 3-day patch and one 4-day patch, two 3.5-day patches, or two 4-day patches, the respective patches are administered every $3^{rd}$ and $4^{th}$ day or every $4^{th}$ and $3^{rd}$ day at two predetermined days per week.

The present invention therefore also provides in a second aspect a kit comprising two transdermal therapeutic systems of the present invention, wherein the two transdermal therapeutic systems may have the same or a different rotigotine content. In one embodiment, the two transdermal therapeutic systems of the kit have a different rotigotine content and one of them is adapted to allow for the transdermal administration of therapeutically effective amounts of rotigotine for at least 3 days and the other one is adapted to allow for the transdermal administration of therapeutically effective amounts of rotigotine for at least 4 days. In a preferred embodiment, the two transdermal therapeutic systems of the kit have the same rotigotine content and each of them is adapted to allow for the transdermal administration of therapeutically effective amounts of rotigotine for at least 4 days.

In a third aspect, the present invention provides a method for preparing the transdermal therapeutic system described herein.

The preparation method of the present invention comprises preparing a rotigotine containing solid dispersion, i.e. the reservoir layer and optionally the skin adhesive layer (if it contains rotigotine) forming the self-adhesive matrix layer, optionally preparing a skin adhesive layer containing no rotigotine, coating, drying or cooling and laminating to get the bulk product, converting the obtained laminate into patches via cutting, and packaging.

Preparing a skin adhesive layer containing no rotigotine, involves the preparation of a solution of one or more adhesive(s), coating this solution on a release liner and drying the resulting laminate.

Coating, drying and laminating as well as converting the obtained laminate into separate patches via cutting and packaging are well known steps in the preparation of transdermal therapeutic systems and these steps can be carried out as described in the prior art. Reference can for example be made to the detailed description of the preparation of the example patches in the international patent application WO 99/49852.

Figure 1:
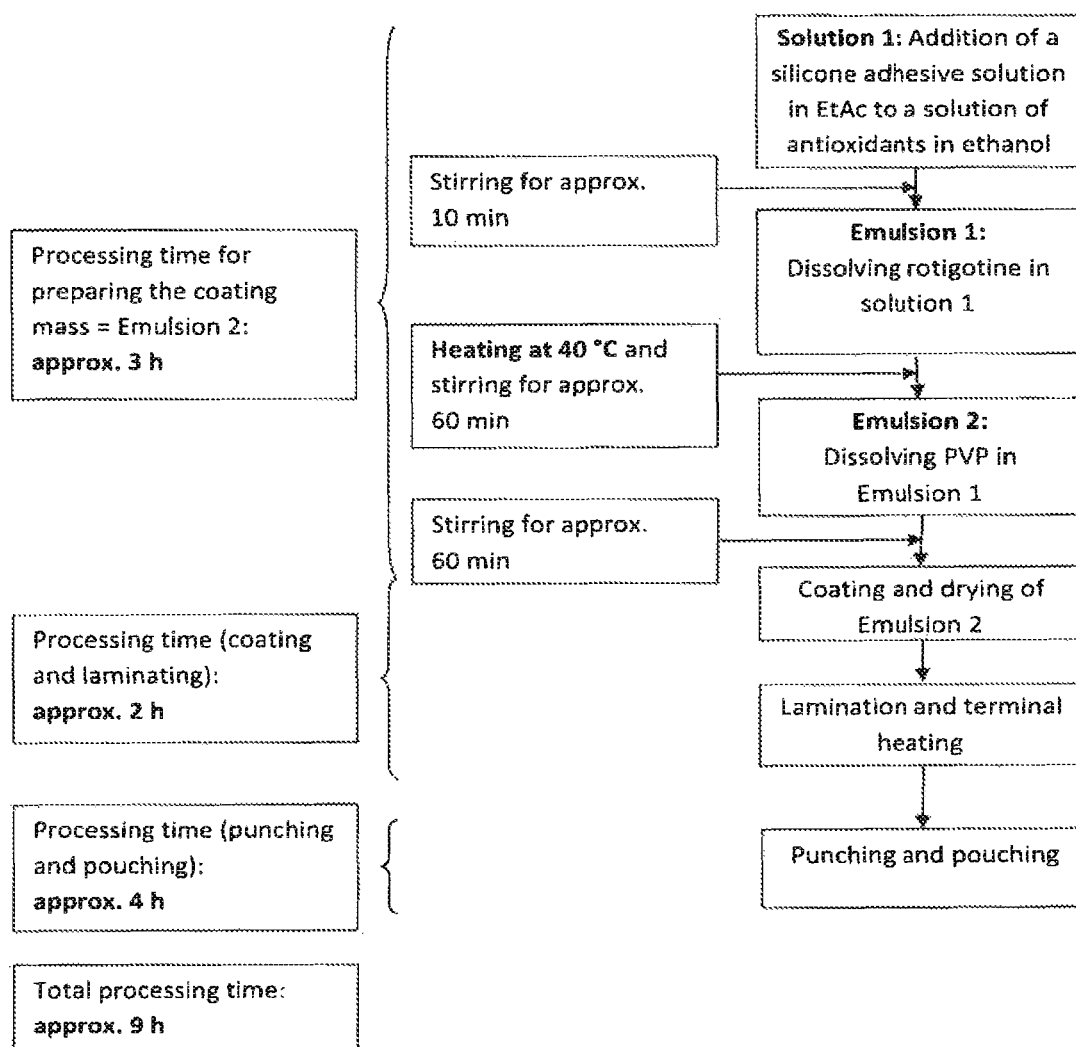
FIG. 1 shows a flow chart of a method for the preparation of a multi-day rotigotine containing patch of the present invention using a solvent system consisting of ethyl acetate and ethanol in a ratio of 5:1 and involving the addition of rotigotine in one portion under heating.
Figure 2A:
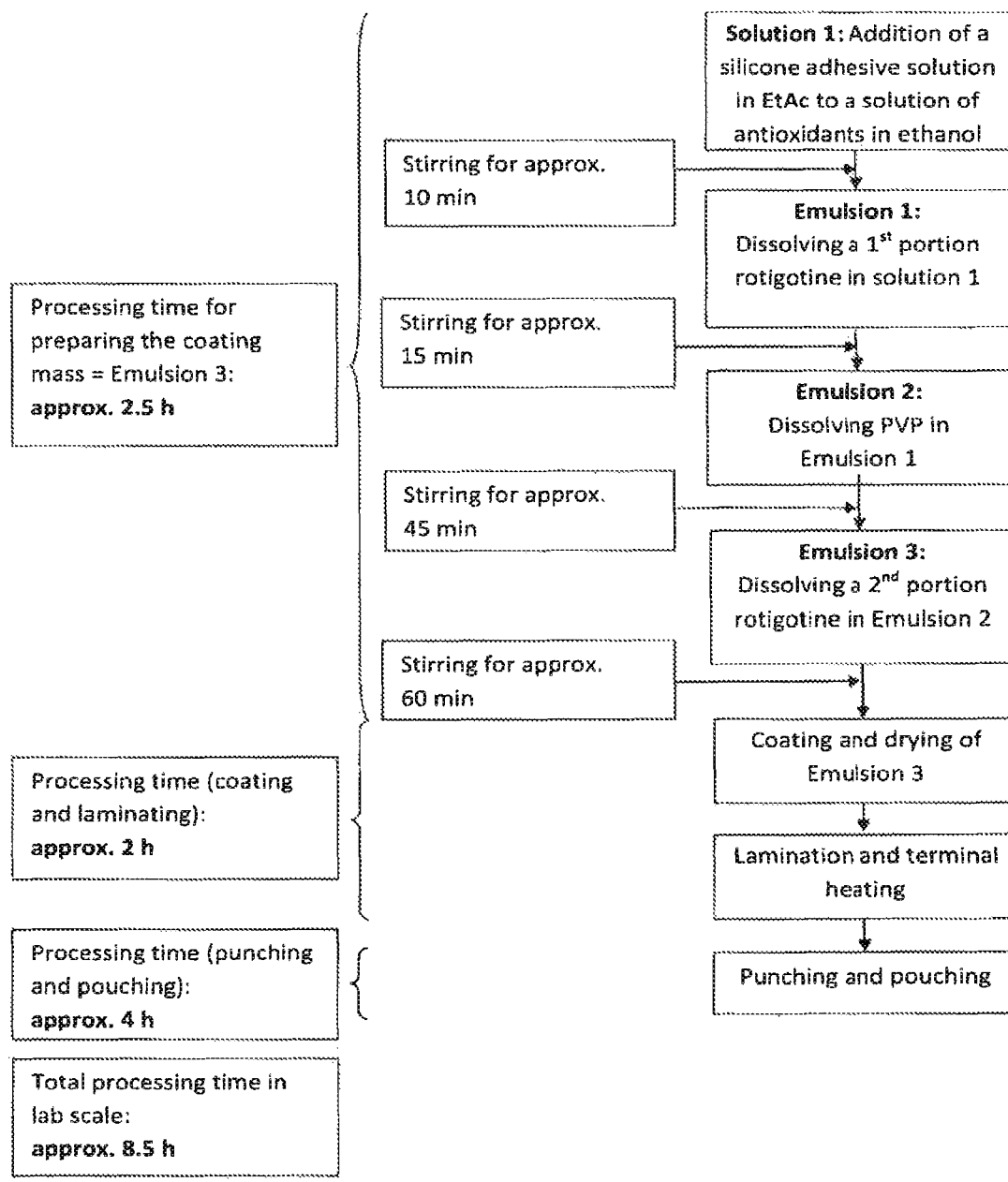
FIG. 2a shows a flow chart of a method for the preparation of a multi-day rotigotine containing patch of the present invention using a solvent system consisting of ethyl acetate and ethanol in a ratio of 5:1 and involving the addition of rotigotine in two portions, one before and the other after PVP is added, at room temperature without heating.
Figure 2B:
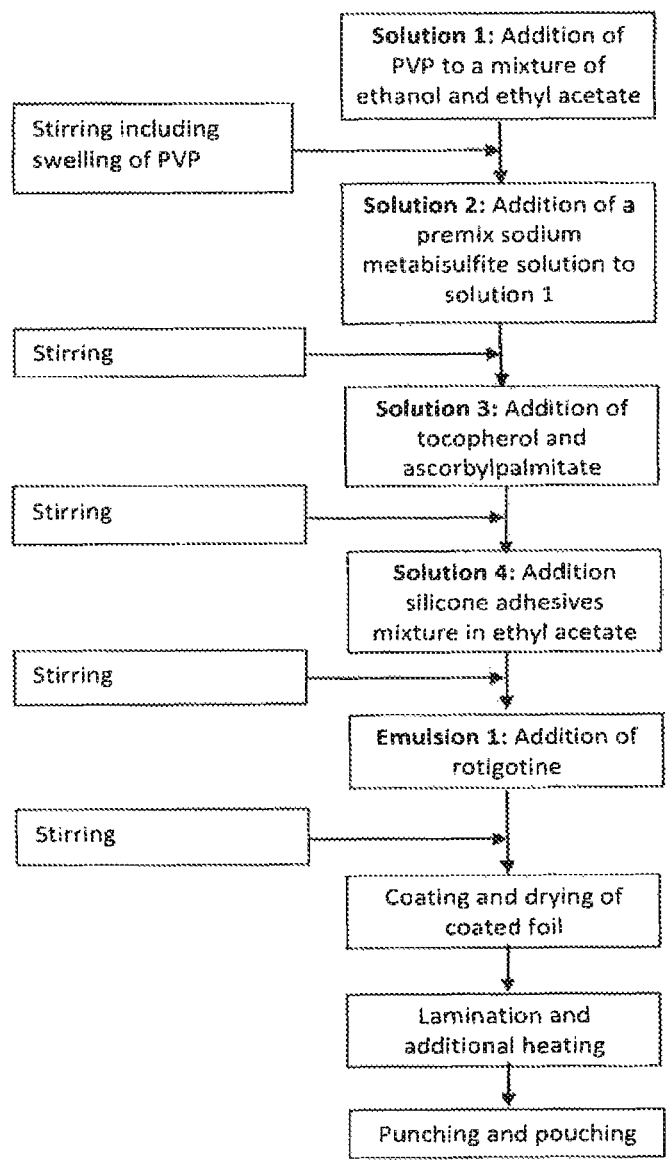
FIG. 2b shows a flow chart of a method for the preparation of a multi-day rotigotine containing patch of the present invention using a solvent system consisting of ethyl acetate and ethanol, involving the addition of rotigotine in one portion to a PVP solution and a silicone adhesives mixture, at room temperature without heating.
Figure 3:
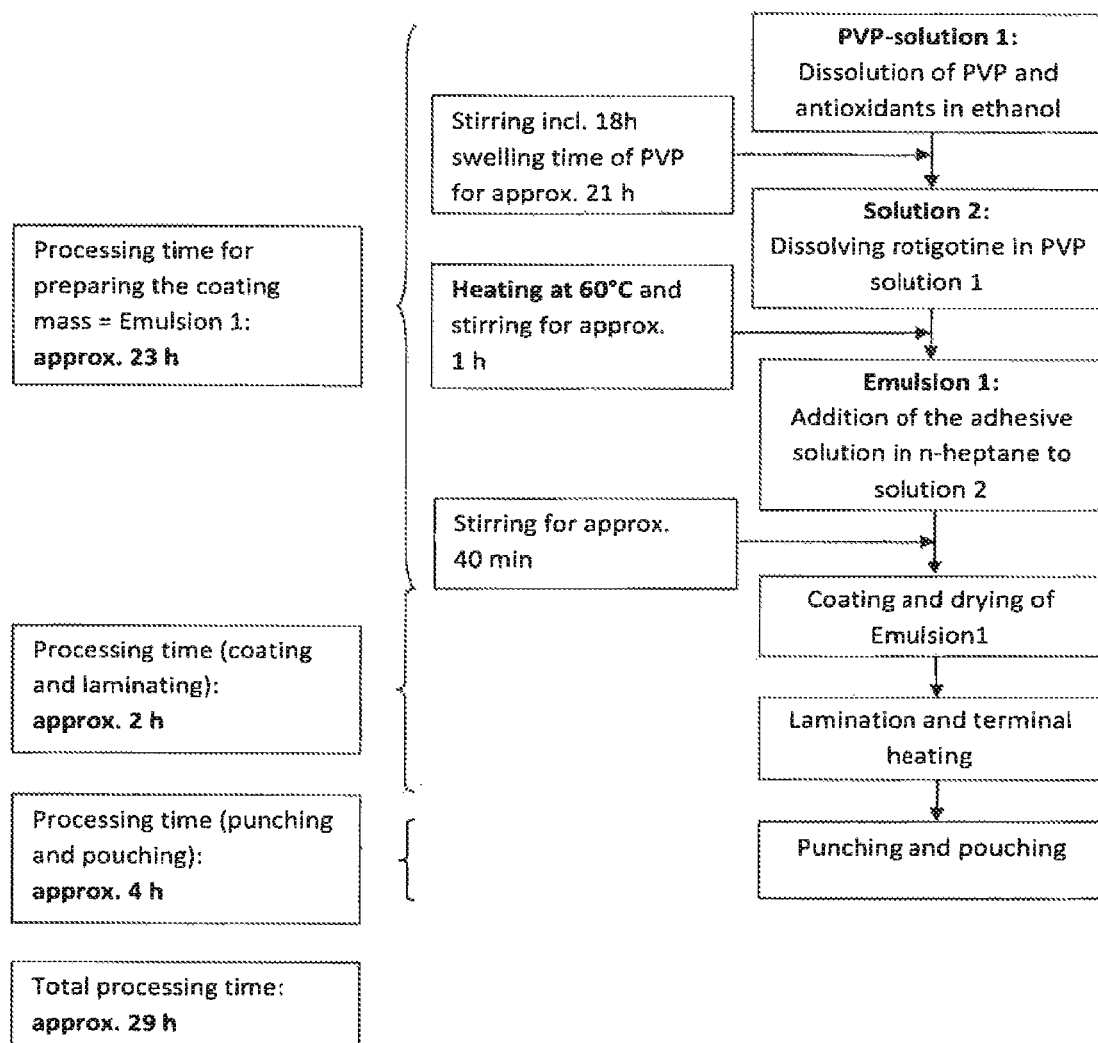
FIG. 3 shows a flow chart of a method for the preparation of a multi-day rotigotine containing patch of the present invention using a solvent system consisting of heptane and ethanol in a ratio of 1:1.5.

The rotigotine containing solid dispersion of the self-adhesive layer of the transdermal therapeutic system of the present invention can be prepared in accordance with one of the methods depicted in the flow charts of FIGS. 1-3.

The preparation methods described therein involve two different solvent systems, one consisting of ethyl acetate and ethanol, like for example in a ratio of 5:1 and the other consisting of heptane and ethanol, like for example in a ratio of 1:1.5.

The comparison between the different preparation methods shown in FIGS. 1-3 reveals that the solvent system consisting of ethyl acetate and ethanol, like for example in a ratio of 5:1 allows for a significant reduction of time needed for incorporating/dissolving PVP and thus in preparing the final patches. This reduction in time is based on the surprising finding that the solubility of PVP in the aprotic polar solvent ethyl acetate is enhanced by rotigotine by one order of magnitude. Moreover, a solvent system consisting of an aprotic polar solvent and a protic polar solvent like the solvent system consisting of ethyl acetate and ethanol, for example in a ratio of 2:1 to 5:1 is required for incorporating high rotigotine concentrations of up to about 18 wt.-% in the self-adhesive matrix layer of the transdermal therapeutic system of the present invention.

In a preferred embodiment, the preparation method of the present invention therefore involves the use of a solvent system consisting of an aprotic polar solvent and a protic polar solvent in a ratio of 2:1 to 9:1. In a more preferred embodiment, the preparation of the present invention involves the use of a solvent system consisting of a aprotic polar solvent and a protic polar solvent in a ratio of 2:1 to 6:1, preferably in a ratio of 2:1 to 5:1, more preferably in a ratio of 3:1 to 5:1, particularly preferred in a ratio of 3:1 or 5:1.

In a more preferred embodiment, the preparation method of the present invention involves the use of a solvent system consisting of a carboxylic acid ester and an aliphatic alcohol. In a particular preferred embodiment, the preparation method of the present invention involves the use of a solvent system consisting of ethyl acetate and ethanol in a ratio of 2:1 to 9:1. In a further preferred embodiment, the preparation method of the present invention involves the use of a solvent system consisting of ethyl acetate and ethanol in a ratio of 2:1 to 6:1, preferably in a ratio of 2:1 to 5:1, more preferably in a ratio of 3:1 to 5:1, particularly preferred in a ratio of 3:1 or 5:1.

The addition of a small portion of ethanol to ethyl acetate enables the formation of rotigotine/PVP droplets in ethyl acetate-based silicone adhesive solutions and allows for homogenously dispersing the rotigotine/PVP conjugate in the silicone adhesive solution at room temperature.

As shown in FIGS. 2a and 2b, the preparation method of the present invention can therefore be carried out at room temperature without heating. When doing so, the method may involve either (i) the addition of rotigotine in two portions, one before and the other after polyvinylpyrrolidone is added to the mixture of silicone adhesives and antioxidants prepared in the solvent system (see FIG. 2a), or (ii) the addition of rotigotine in one portion together with polyvinylpyrrolidone to the mixture of silicone adhesives and antioxidants prepared in the solvent system or (iii) the addition of rotigotine in one portion to a PVP solution and a silicone adhesives mixture (see FIG. 2b).

Thus, in a further preferred embodiment, the preparation method of the present invention is carried out at room temperature and involves the addition of rotigotine in two portions, one before and the other after polyvinylpyrrolidone is added or in another preferred embodiment the addition of rotigotine in one step and the use of a polyvinylpyrrolidone solution and silicone adhesives mixture When adding rotigotine in one portion before polyvinylpyrrolidone is added, moderate heating to about 40° C. may be useful (FIG. 1). However, this does not have any influence on the reduced time needed for the subsequent incorporation/dissolution of PVP, which is carried out at room temperature.

In a another embodiment of the present invention, the preparation method for the preparation of a transdermal therapeutic system comprising
(a) a backing layer,
(b) a solvent-based self-adhesive matrix layer containing rotigotine as active ingredient, and
(c) a release liner,
comprises the steps of
i) addition of polyvinylpyrrolidone to a mixture of carboxylic acid ester and an aliphatic alcohol, preferably ethyl acetate and ethanol,
ii) addition of sodium metabilsufite solution to mixture of step i,
iii) addition of tocopherol and ascorbylpalmitate to mixture of step ii,
iv) combining of mixture of step iii with a mixture of silicone adhesives in carboxylic acid ester, preferably ethyl acetate,
v) addition of rotigotine to combination of step iv,
vi) coating of the mixture of step v onto a substrate, preferably the release liner and removal of the solvents to obtain the reservoir layer thereby forming the solvent-based self-adhesive matrix layer,
vii) lamination of reservoir layer from step vi with a cover layer, preferably backing layer and
viii) punching of laminate from step vii into individual transdermal therapeutic systems.

In a further embodiment, the preparation method of the present invention involves the use of a solvent system consisting of heptane and ethanol in a ratio of 1.5:1 to 1:1.5, more preferred in a ratio of 1.4:1 and particularly preferred in a ratio of 1:1.5. A preparation method of the present invention, wherein a solvent system consisting of heptane and ethanol in a ratio of 1:1.5 is used, is shown FIG. 3.

The water content in the final patches obtained by the preparation method of the present invention is in general low enough so that no evaporation of water during preparation of the patches is necessary. Typically, the water content in a freshly prepared patch is below about 2 wt.-%.

In one embodiment, the water content of the transdermal therapeutic system of the present invention therefore is below about 2 wt.-%, preferably below about 1 wt.-% and more preferred below about 0.6 wt.-%.

For preparing the transdermal therapeutic system of the present invention, either of the two crystalline forms of rotigotine, i.e. polymorphic Form I or polymorphic Form II, may be employed as a starting material.

In a preferred embodiment, rotigotine of polymorphic Form II is used as starting material for preparing the transdermal therapeutic system of the present invention.

Based on the above described dosage regimens, the present invention provides in another aspect a transdermal therapeutic system comprising rotigotine as active ingredient for use in the treatment of patients suffering from Parkinson's disease, Parkinson's plus syndrome, depression, fibromyalgia and the restless-legs syndrome and for use in the treatment or prevention of dopaminergic neuron loss or cognitive disorders following stroke by transdermal administration of rotigotine once or twice weekly, wherein the transdermal therapeutic system comprises a backing layer, a solvent-based rotigotine containing self-adhesive matrix layer as well as a release liner and is adapted to allow for the transdermal administration of therapeutically effective amounts of rotigotine for at least 3 days.

All aspects, embodiments and preferred embodiments as well as combinations thereof described in the foregoing for the transdermal therapeutic system of the present invention also apply to the rotigotine-containing transdermal therapeutic system for use according to the forth aspect of the present invention.

The invention and the best mode for carrying it out will be explained in more detail in the following non-limiting examples.

EXAMPLES

Example 1

4-Day mono-layer TTS comprising a reservoir layer having a coating weight of 150 g/m² and containing 9 wt.-% rotigotine and 2 wt.-% PVP; solvent system used for the preparation method: heptane/ethanol (1.4:1 (w/w))

18.44 kg silicone adhesive 7-4301 (73 wt.-% in heptane) were mixed with the following components under permanent stirring until a homogeneous dispersion was obtained:
1. 2.44 kg of an ethanolic solution containing 25 wt.-% polyvinylpyrrolidone (Kollidon F 90), 0.11 wt.-% aqueous sodium metabisulfite solution (10 wt.-%), 0.25 wt.-% ascorbyl palmitate and 0.62 wt.-% DL-alpha-tocopherol;
2. 9.131 kg of an ethanolic solution containing 2.724 kg rotigotine obtained by dissolving rotigotine of polymorphic Form I;
3. 18.43 kg of silicone adhesive 7-4201 (73 wt.-% in heptane); and
4. 1.579 kg heptane.

For the manufacture of the self-adhesive matrix layer, the obtained dispersion was coated onto a suitable release liner (e.g. Scotchpak™ 9744) and the solvents were continuously removed in a drying oven at temperatures up to 80° C. in order to obtain a dry drug containing matrix having a coating weight of 150 g/m². The dried matrix layer was then laminated with a polyester-type backing foil being siliconized on the inner surface and aluminium vapor coated on the opposite surface.

Finally, individual patches having a size of 10 cm² were punched out of the obtained laminate and were sealed into pouches under nitrogen flow.

Example 2

7-Day bi-layer TTS comprising (a) a reservoir layer having a coating weight of 150 g/m² and containing 18 wt.-% rotigotine and 4 wt.-% PVP and (b) a skin adhesive layer containing no rotigotine and having a coating weight of 18 g/m²; solvent system used for the preparation method: heptane/ethanol (1.4:1 (w/w))

Preparation of the Reservoir Layer Matrix (Step 1)

9.66 kg silicone adhesive 7-4301 (73 wt.-% in heptane) were mixed with the following components under permanent stirring until a homogeneous dispersion was obtained:
1. 2.90 kg of an ethanolic solution containing 25 wt.-% polyvinylpyrrolidone (Kollidon F 90), 0.11 wt.-% aqueous sodium metabisulfite solution (10 wt.-%), 0.25 wt.-% ascorbyl palmitate and 0.62 wt.-% DL-alpha-tocopherol;
2. 6.98 kg of an ethanolic solution containing 3.26 kg rotigotine obtained by dissolving rotigotine of polymorphic Form I;
3. 9.66 kg of silicone adhesive 7-4201 (73 wt.-% in heptane); and
4. 0.82 kg heptane.

Preparation of the Skin Adhesive Layer (Step 2)

11.51 kg silicone adhesive 7-4301 (73 wt.-% in heptane) were mixed with 7.67 kg silicone adhesive 7-4201 (73 wt.-% in heptane) and 0.82 kg heptane. The adhesive solution was then coated onto a suitable polyester release liner (e.g. Scotchpak™ 9744) up to a coating weight of 18 g/m². The solvent was continuously removed in a drying oven at a temperature of up to 80° C. (±3° C.) to obtain a dry adhesive film having a coating weight of 18 g/m².

Preparation of the Final TTS (Step 3)

The dispersion obtained in Step 1 was coated onto two sheets of a suitable polyester release liner (e.g. Scotchpak™ 9744) to obtain two drug-containing reservoir layers each having a coating weight of 75 g/m². The coated release liner sheets were placed in a drying oven and dried at a temperature of up to 80° C. (±3° C.) to obtain two dry adhesive films each having a coating weight of 75 g/m². The first dried drug-containing reservoir layer was laminated with (1) a polyester-type backing foil being siliconized on the inner surface and aluminium vapor coated on the opposite surface and (2) the second drug-containing reservoir layer after removal of the release liner from the surface of the first reservoir layer to be laminated in order to obtain a drug-containing reservoir layer having a coating weight of 150 g/m².

Afterwards, the skin adhesive layer was laminated with the drug-containing reservoir layer after removal of its release liner to obtain a laminate consisting of a backing foil, a rotigotine-containing reservoir layer having a coating weight of 150 g/m², a skin adhesive layer having a coating weight of 18 g/m² and a release liner. The whole laminate was dried at a temperature of up to 80° C. (±3° C.). Finally, individual patches having a size of 10 cm² were punched out of the complete laminate and sealed into pouches.

Comparative Example 1

Single-day mono-layer TTS comprising a reservoir layer having a coating weight of 50 g/m² and containing 9 wt.-% rotigotine and 2 wt.-% PVP; solvent system used for the preparation method: heptane/ethanol (1.4:1 (w/w))

The patches of Comparative Example 1 were manufactured according to the method described in Example 1, but with a coating weight of 50 g/m² instead of 150 g/m².

The composition of the patches of Examples 1 and 2 as well as Comparative Example 1 are depicted in Table 3.

TABLE 3

Composition of the patches of Examples 1 and 2 and Comparative Example 1

| Ingredient [mg/10 cm²], except stated otherwise | | Example Ex. 1 | Ex. 2 | Comp. Ex. 1 |
|---|---|---|---|---|
| Reservoir layer | Rotigotine (Form I*) | 13.5 | 27.0 | 4.5 |
| | Rotigotine (Form I*) content [wt.-%] | 9.0 | 18.0 | 9.0 |
| | PVP | 3.0 | 6.0 | 1.0 |
| | PVP content [wt.-%] | 2.0 | 4.0 | 2.0 |

TABLE 3-continued

Composition of the patches of Examples 1 and 2 and Comparative Example 1

| | Ingredient [mg/10 cm²], except stated otherwise | Ex. 1 | Ex. 2 | Comp. Ex. 1 |
|---|---|---|---|---|
| | Rotigotine:PVP ratio [wt.-%] | 9:2 | 18:4 | 9:2 |
| | Silicone adhesive 7-4301 | 66.7 | 58.39 | 22.24 |
| | Silicone adhesive 7-4201 | 66.7 | 58.39 | 22.23 |
| | Sodium metabisulfite | 0.00133 | 0.00264 | 0.00045 |
| | Ascorbyl palmitate | 0.030 | 0.060 | 0.01 |
| | DL-α-Tocopherol | 0.075 | 0.150 | 0.025 |
| | Coating weight [g/m²] | 150.0 | 150.0 | 50.0 |
| Skin adhesive layer | Rotigotine (Form I*) | — | — | — |
| | Rotigotine (Form I*) content [wt.-%] | — | — | — |
| | PVP | — | — | — |
| | PVP content [wt.-%] | — | — | — |
| | Rotigotine:PVP ratio [wt.-%] | — | — | — |
| | Silicone adhesive 7-4301 | — | 10.8 | — |
| | Silicone adhesive 7-4201 | — | 7.2 | — |
| | Sodium metabisulfite | — | — | — |
| | Ascorbyl palmitate | — | — | — |
| | DL-α-Tocopherol | — | — | — |
| | Coating weight [g/m²] | — | 18.0 | — |

*For the preparation of the respective example patches rotigotine of polymorphic Form I was used as starting material. The final patches contain rotigotine in non-crystalline form.

In Vivo Drug Absorption Test

In order to monitor the absorption of rotigotine by the human skin using the transdermal therapeutic systems of Examples 1 and 2 and Comparative Example 1 two pilot bioavailability (BA) studies over 4 days (Study 1) and 7 days (Study 2), respectively, were carried out.

Study 1

A single application of one TTS of Example 1 for 4 days was compared in healthy male subjects with a once-daily application of the TTS of Comparative Example 1 over 4 days in a single-site, open-label, randomized, crossover trial to evaluate the pharmacokinetics of the two different patch formulations. Subjects received one patch of Example 1 for 4 days (Treatment A) or four single patches of Comparative Example 1 at 4 consecutive days (Treatment B) in a randomized sequence (A-B or B-A). Individual rotigotine plasma concentrations were analysed for 12 subjects by means of liquid chromatography and mass spectroscopy. The lower limit of quantification (LOQ) was 0.01 ng/ml.

Study 2

A single application of one TTS of Example 2 for 7 days was compared in healthy male subjects with a once-daily application of the TTS of Comparative Example 1 over 7 days in a single-site, open-label, randomized, crossover trial to evaluate the pharmacokinetics of the two different patch formulations. Subjects received one patch of Example 2 for 7 days (Treatment C) or seven single patches of Comparative Example 1 at 7 consecutive days (Treatment D) in a randomized sequence (C-D or D-C). Individual rotigotine plasma concentrations were analysed for 16 subjects by means of liquid chromatography and mass spectroscopy. The lower limit of quantification (LOQ) was 0.01 ng/ml.

In addition the residual drug content remaining in the patches after application in Study 1 was determined by a validated HPLC method. From these data the mean apparent dose which was released by the patch to the skin application site was estimated by the difference between declared drug content of the patch and its mean content after removal from the skin.

The in vivo drug absorption was calculated from the plasma concentration data according to the Wagner-Nelson method (Malcom Rowland, Thomas N. Tozer (Eds.) "Estimation of Adsorption Kinetics from Plasma Concentration Data" in Clinical Phamacokinetics, pp. 480-483, Williams & Wilkins, 1995); 100%=absorption rate measured after 4 days.

Results—Plasma Concentration Time Profiles

Figure 4A:
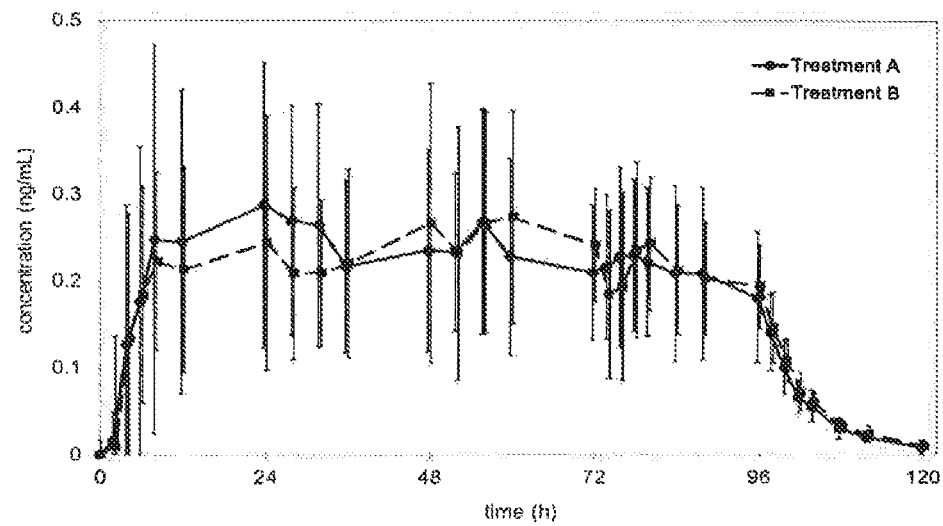
FIG. 4a shows the plasma concentration time profiles of rotigotine over 4 days after the administration of one 4-day mono-layer TTS of Example 1 (Treatment A) in comparison to the daily administration of four 1-day patches of Comparative Example 1 (Treatment B) (n=12).

The plasma concentration time profiles measured for Treatments A and B in Study 1 are depicted in FIG. 4a. The administration of a single 4-day patch manufactured as described under Example 1 was found to be bioequivalent to the daily administration of 4 single-day patches of Comparative Example 1.

The administration of a single 7-day patch manufactured as described under Example 2 (Treatment C) was found in Study 2 to be almost bioequivalent to the daily administration of 7 single-day patches of Comparative Example 1 (Treatment D), although only 27 mg of rotigotine were administered by the 7-day patch of Example 2 instead of 7×4.5 mg, i.e. 31.5 mg, rotigotine, which were administered by 7 single-day patches of Comparative Example 1. That is, one daily dose of rotigotine of 4.5 mg could be saved during Treatment C in comparison to Treatment D.

Upon normalization by the apparent dose, the values for AUC and $C_{max}$ showed a supra bioavailability, i.e. an appreciably larger bioavailability, of 120% for the AUC and 126% for $C_{max}$.

When the rotigotine content of a 7-day patch was adapted in accordance with the rotigotine content of 7 single-day patches, subjects/patients would thus receive about 20% more rotigotine than could be expected based on the bioavailability of rotigotine upon administration by a single-day patch.

Figure 4B:
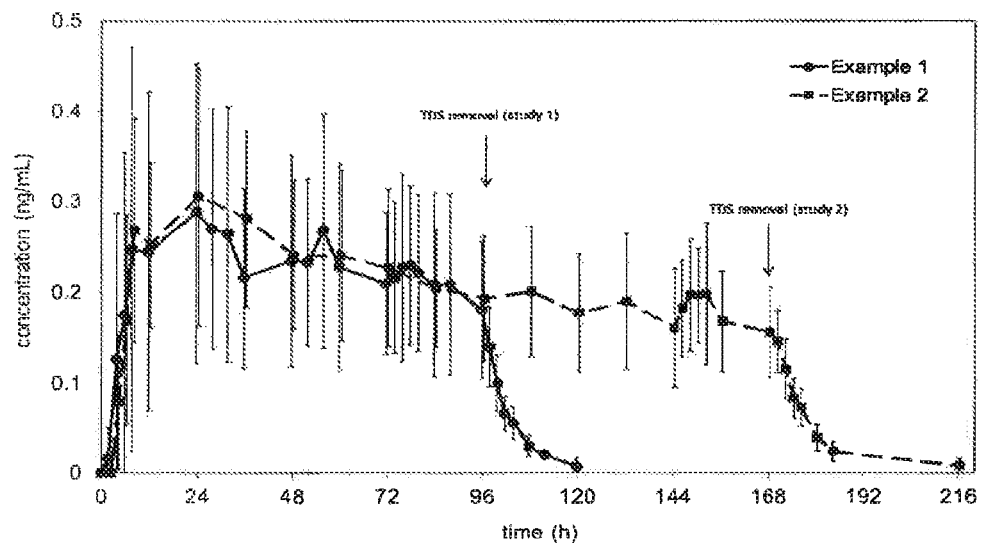
FIG. 4b shows the plasma concentration time profiles of rotigotine after the administration of one 4-day mono-layer TTS of Example 1 (Treatment A, n=12) and one 7-day bi-layer TTS of Example 2 (Treatment C, n=16).

The plasma concentration time profiles measured for the 4-day patch of Example 1 in Study 1 and for the 7-day patch of Example 2 in Study 2 are depicted in FIG. 4b.

By comparing the variations of the mean plasma concentrations within one day for the single and the once daily application over 4 and 7 days, it becomes evident that the mean plasma concentrations of the multi-day patches of Examples 1 and 2 are on average characterized by fewer fluctuations within a 24 h interval than the mean plasma concentrations obtained for the once daily administered patches of Comparative Example 1. That is, due to the removal of one patch and the consecutive application of a fresh patch onto another skin application site, the daily administration of the patches of Comparative Example 1 apparently led to larger variations.

Figure 5A:
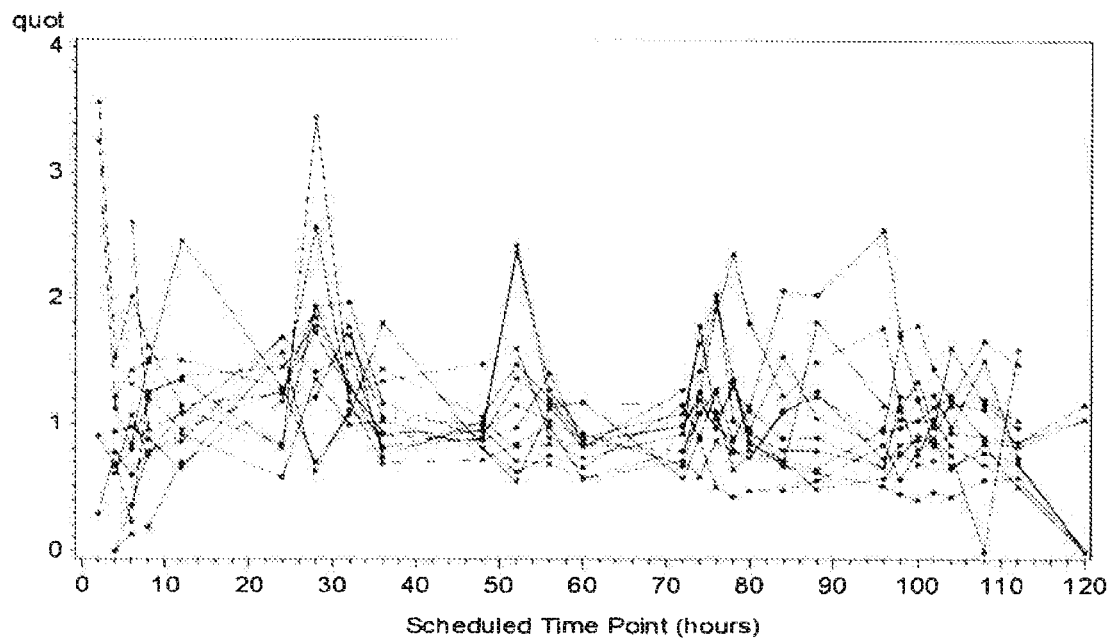
FIG. 5a shows the individual rotigotine plasma concentration ratios over 4 days obtained after the single administration of the 4-day mono-layer TTS of Example 1 in comparison to the once daily application of four 1-day patches of Comparative Example 1 in Study 1 (n=12).
Figure 5B:
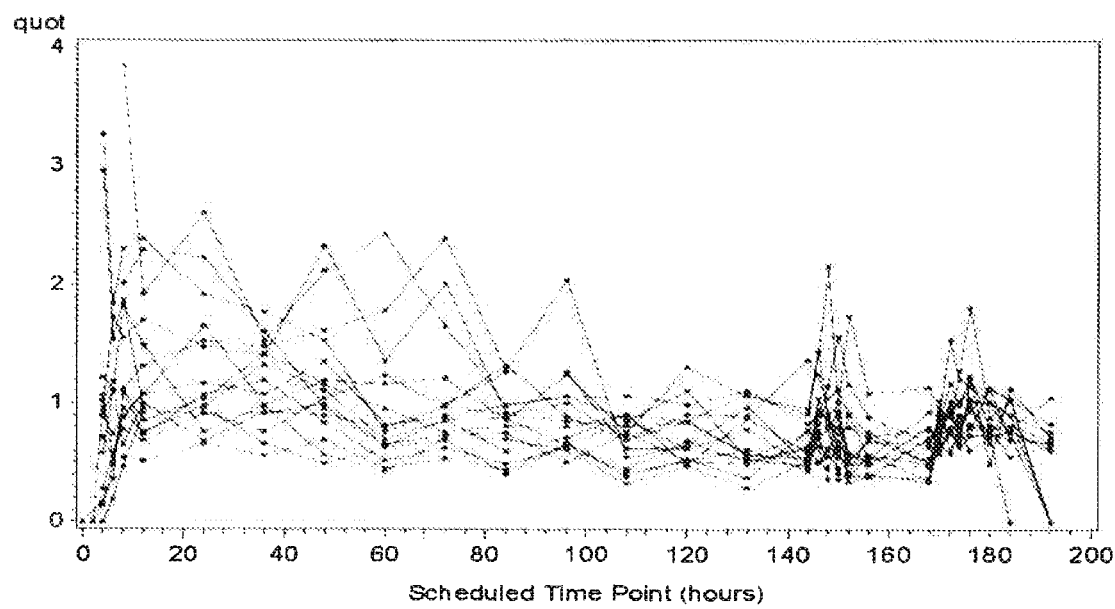
FIG. 5b shows the individual rotigotine plasma concentration ratios over 7 days obtained after the single administration of the 7-day bi-layer TTS of Example 2 in comparison to the once daily application of seven 1-day patches of Comparative Example 1 in Study 2 (n=16).

Accordingly, individual plasma concentrations measured over 4 and 7 days after the single administration of the multi-day patches of Examples 1 and 2 and after the daily administration of four or seven single-day patches of Comparative Example 1 at the time of patch replacement of the single day patches of Comparative Example 1 were found to be consistently higher for the multi-day patches of Examples 1 and 2 in most cases. Consequently, as shown in FIGS. 5a and 5b, the rotigotine plasma concentration ratio of the patch of Example 1 to the patches of Comparative Example 1 and of the patch of Example 2 to the patches of Comparative Example 1 was above 1 during the 4-day treatment as well as during the 7-day treatment for the majority of subjects.

Results—Apparent Dose Determination

The mean apparent drug doses released to the skin in BA Study 1 as well as the mean drug depletion rate calculated on the basis of the nominal rotigotine content in the respective patches are shown in Table 4a. The applied total dose, i.e. the nominal rotigotine content of the applied patches, as well as the mean drug quantity saved by the multi-day patch of Example 1 in comparison to the 4 single-day patches of Comparative Example 1 are shown in Table 4b.

TABLE 4a

Result of apparent dose determinations (=estimated drug release in vivo) and corresponding mean depletion rates in BA Study 1

| Sample | Mean apparent dose [mg/10 cm$^2$] over 4 days | SD | Mean depletion rate [%] | n |
|---|---|---|---|---|
| Example 1 (Treatment A) | 7.5 | 2.5 | 55.6 | 12 |
| Comparative Example 1 (Treatment B) | 8.7 | 2.1 | 48.6 | 12 |

TABLE 4b

Comparison of the total (nominal) rotigotine doses applied during Treatment A and Treatment B in BA Study 1 and corresponding mean drug quantity saved by the multi-day patch of Example 1 in comparison to the 4 single-day patches of Comparative Example 1

| Sample | Applied total dose [mg/10 cm$^2$] (=total (nominal) drug content of the patch(es)) | Coating weight 150 [g/m$^2$] | Mean drug quantity saved by Treatment A in comparison to Treatment B | n |
|---|---|---|---|---|
| Example 1 (Treatment A) | 13.5 | 150 | 4.5 mg/4 d 1.1 mg/24 h | 12 |
| Comparative Example 1 (Treatment B) | 18.0 | 50 | —/— | 12 |

Despite a lower mean apparent dose delivered by the TTS of Example 1, bioequivalence to the daily application of 4 patches of Comparative Example 1 over 4 days could be demonstrated. This observation indicates that the daily administration of a single-day TTS requires more drug than the single administration of one multi-day TTS over the same period of time for obtaining bioequivalent rotigotine plasma concentrations. From the difference in the mean apparent dose between the two bioequivalent medications shown in Table 4a the mean additional need of rotigotine drug substance for the once daily administration with single-day patches can be estimated to be approximately 0.4 mg/10 cm$^2$/day in the steady state.

Tolerability and Skin Adhesiveness

In BA Studies 1 and 2, the patches of Examples 1 and 2 as well as Comparative Example 1 were generally well tolerated. Skin tolerability and adhesiveness of all patches were good during either treatment.

Surprisingly, incidence of overall adverse effects was lower for the single administration of the multi-day patches of Examples 1 and 2 compared to the daily administration of the single-day patches of Comparative Example 1. As such, the pilot BA studies did not indicate any inferiority concerning tolerability of the multi-day transdermal therapeutic systems of the present invention in comparison to the daily administration of conventional single-day transdermal therapeutic systems.

Good adhesiveness of the multi-day patches of Example 1 having a coating weight of 150 g/m$^2$ and Example 2 having a coating weight of 168 g/m$^2$ in vivo was consistent with good peel adhesion properties observed in vitro.

Example 3

7-Day bi-layer TTS comprising (a) a reservoir layer having a coating weight of 150 g/m$^2$ and containing 18 wt.-% rotigotine and 8 wt.-% PVP and (b) a skin adhesive layer containing no rotigotine and having a coating weight of 18 g/m$^2$; solvent system used for the preparation method: ethyl acetate/ethanol (5:1 (w/w))

Preparation of the Reservoir Layer Matrix (Step 1)

0.061 g DL-α-Tocopherol, 0.024 g ascorbyl palmitate and 0.020 g of an aqueous sodium metabisulfite solution (10 wt.-%) were mixed with 6.0 g anhydrous ethanol to obtain a clear solution.

38.0 g silicone adhesive 7-4202 (59.1 wt.-% in ethyl acetate) and 36.9 g silicone adhesive 7-4302 (60.9 wt.-% in ethyl acetate) were added to the obtained solution of antioxidants and stirred at 400 rpm. After approximately 10 min, 11.0 g rotigotine of polymorphic Form II were added while stirring. The mixture was heated up to 40° C. and stirred at 400 rpm until a homogenous dispersion was obtained. Thereafter 4.9 g polyvinyl pyrrolidone (Kollidon 90F) were added to this mixture while stirring. The mixture was stirred at 600 rpm until a homogeneous dispersion was obtained.

Preparation of the Skin Adhesive Layer (Step 2)

33.84 g of silicone adhesive 7-4202 (59.1 wt.-% in ethyl acetate) were mixed with 49.26 g of silicone adhesive 7-4302 (60.9 wt.-% in ethyl acetate). The adhesive solution was then coated onto a suitable polyester release liner (e.g. Scotchpak™ 9744) up to a coating weight of 18 g/m$^2$. The coated release liner was placed in a drying oven and dried at 50° C. for about 30 min and at 115° C. for about 10 min.

Preparation of the Final TTS (Step 3)

The dispersion obtained in Step 1 was coated onto two sheets of a suitable polyester release liner (e.g. Scotchpak™ 9744) to obtain two drug-containing reservoir layers each having a coating weight of 75 g/m$^2$. The coated release liner sheets were placed in a drying oven and dried at 50° C. for about 30 min and then at 115° C. for about 10 min. The first dried drug-containing reservoir layer was laminated with (1) a polyester-type backing foil and (2) the second drug-containing reservoir layer after removal of the release liner from the surface of the first reservoir layer to be laminated in order to obtain a drug-containing reservoir layer having a coating weight of 150 g/m$^2$.

The lamination with only (1) a polyester-type backing foil results in only one drug-containing reservoir layer having a coating weight of 75 g/m$^2$ which leads to a transdermal therapeutic system with a shorter application time of exemplarily 3.5 days.

Afterwards, the skin adhesive layer was laminated with the drug-containing reservoir layer after removal of its release liner to obtain a laminate consisting of a backing foil, a rotigotine-containing reservoir layer having a coating weight of 150 g/m$^2$, a skin adhesive layer having a coating weight of 18 g/m$^2$ and a release liner. The whole laminate was dried at a temperature of 115° C. for about 10 min. Finally, individual patches having a size of 10 cm$^2$ were punched out of the complete laminate and sealed into pouches.

Example 4

7-Day mono-layer TTS comprising a reservoir layer having a coating weight of 150 g/m² and containing 18 wt.-% rotigotine and 8 wt.-% PVP; solvent system used for the preparation method: ethyl acetate/ethanol (5:1 (w/w))

The patches of Example 4 were manufactured according to the method described in Example 3, but without adding a skin adhesive layer.

Example 5

7-Day mono-layer TTS comprising a reservoir layer having a coating weight of 300 g/m² and containing 9 wt.-% rotigotine and 4 wt.-% PVP; solvent system used for the preparation method: ethyl acetate/ethanol (5:1 (w/w))

Preparation of the Reservoir Layer Matrix (Step 1)

0.030 g DL-α-Tocopherol, 0.012 g ascorbyl palmitate and 0,010 g of an aqueous sodium metabisulfite solution (10 wt.-%) were mixed with 7.1 g anhydrous ethanol to obtain a clear solution.

44.7 g silicone adhesive 7-4202 (59.1 wt.-% in ethyl acetate) and 43.4 g silicone adhesive 7-4302 (60.9 wt.-% in ethyl acetate) were added to the above solution of antioxidants and stirred at 400 rpm. After approximately 10 min, 5.5 g rotigotine of polymorphic Form II were added while stirring. The mixture was heated up to 40° C. and stirred at 400 rpm until a homogenous dispersion was obtained. Thereafter, 2.4 g polyvinyl pyrrolidone (Kollidon 90F) were added to this mixture while stirring. The mixture was stirred at 600 rpm until a homogeneous dispersion was obtained.

Preparation of the Final TTS (Step 2)

The dispersion obtained in Step 1 was coated onto 4 sheets of a suitable polyester release liner (e.g. Scotchpak™ 9744) to obtain 4 drug-containing reservoir layers each having a coating weight of 75 g/m². The coated release liner sheets were placed in a drying oven and dried at 50° C. for about 30 min and then at 115° C. for about 10 min. The first dried drug-containing reservoir layer was laminated with a polyester-type backing foil on one side and, consecutively, with the 3 remaining drug-containing reservoir layers on the other side after removing the release liner foils from the surface to be laminated of the respective reservoir layers in order to obtain a laminate consisting of a backing foil, a drug-containing reservoir layer having a coating weight of 300 g/m² and a release liner. The whole laminate was dried at a temperature of 115° C. for about 10 min. Finally, individual patches having a size of 10 cm² were punched out of the complete laminate and sealed into pouches.

Example 6

7-Day mono-layer TTS comprising a reservoir layer having a coating weight of 300 g/m² and containing 9 wt.-% rotigotine and 4 wt.-% PVP; solvent system used for the preparation method: heptane/ethanol (1:1.5 (w/w))

Preparation of the Reservoir Layer Matrix (Step 1)

To 19.0 g of an ethanolic PVP solution (containing 12.8 wt.-% polyvinylpyrrolidone (Kollidon 90F), 0.06 wt.-% aqueous sodium metabisulfite solution (10 wt.-%), 0.06 wt.-% ascorbyl palmitate and 0.16 wt.-% DL-alpha-tocopherol), 5.5 g of rotigotine of polymorphic Form II were added. The mixture was stirred for 1.5 h at 60° C. Then, 36.0 g of silicone adhesive 7-4201 (73.6 wt.-% in heptane) and 36.1 g of silicone adhesive 7-4301 (73.3 wt.-% in heptane) were added and the mixture was stirred without heating until a homogeneous dispersion was obtained.

Preparation of the Final TTS (Step 2)

The final patches of Example 6 were manufactured according to the method described in Step 2 of Example 5.

Example 7

7-Day bi-layer TTS comprising (a) a reservoir layer having a coating weight of 100 g/m² and containing 18 wt.-% rotigotine and 8 wt.-% PVP and (b) a skin adhesive layer having a coating weight of 100 g/m² and containing 9 wt.-% rotigotine and 4 wt.-% PVP ("gradient system"); solvent system used for the preparation method: ethyl acetate/ethanol (5:1 (w/w))

Preparation of the Reservoir Layer Matrix (Step 1)

The reservoir layer was manufactured according to the method described in Step 1 of Example 3.

Preparation of the Skin Adhesive Layer (Step 2)

The skin adhesive layer was manufactured according to the method described for the reservoir layer matrix in Step 1 of Example 5.

Preparation of the Final TTS (Step 3)

The final patches of Example 7 were manufactured according to the method described in Step 3 of Example 3, but with only one coating step for each of the reservoir layer and the drug-containing skin adhesive layer resulting in a coating weight of 100 g/m² for each of the two layers.

Example 8

7-Day mono-layer TTS comprising a reservoir layer having a coating weight of 150 g/m² and containing 18 wt.-% rotigotine and 8 wt.-% PVP; solvent system used for the preparation method: ethyl acetate/ethanol (5:1 (w/w)); solubilizing rotigotine and PVP without heating; adding rotigotine in 2 portions before and after the addition of PVP Preparation of the Reservoir Layer Matrix (Step 1)

0.061 g DL-α-Tocopherol, 0.024 g ascorbyl palmitate and 0.020 g of an aqueous sodium metabisulfite solution (10 wt.-%) were mixed with 6.0 g anhydrous ethanol to obtain a clear solution.

38.0 g silicone adhesive 7-4202 (59.1 wt.-% in ethyl acetate) and 36.9 g silicone adhesive 7-4302 (60.9 wt.-% in ethyl acetate) were added to the obtained solution of antioxidants and stirred at 400 rpm. After approximately 10 min, 5.0 g rotigotine of polymorphic Form II were added while stirring at 400 rpm until a homogenous dispersion was obtained (approx. 15 min). Thereafter, 4.9 g polyvinylpyrrolidone (Kollidon 90F) were added to this mixture while stirring at 600 rpm until a homogeneous dispersion was obtained (approx. 45 min). Then, 6.0 g rotigotine of polymorphic Form II were added to the mixture while stirring at 600 rpm until a homogeneous dispersion was obtained (approx. 60 min).

Preparation of the Final TTS (Step 2)

The final patches of Example 8 were manufactured according to the method described in Step 3 of Example 3, but without adding a skin adhesive layer.

Example 9

7-Day mono-layer TTS comprising a reservoir layer having a coating weight of 150 g/m² and containing 18 wt.-% rotigotine and 8 wt.-% PVP; solvent system used for the preparation method: ethyl acetate/ethanol (3:1 (w/w)).

Preparation of the Reservoir Layer Matrix (Step 1)

To 19.6 g of an ethanolic PVP solution (containing 23.5 wt.-% polyvinylpyrrolidone (Kollidon 90F), 0.12 wt.-% aqueous sodium metabisulfite solution (10 wt.-%), 0.12 wt.-% ascorbyl palmitate and 0.29 wt.-% DL-alpha-tocopherol and 21.4 wt-% ethyl acetate), 35.6 g of silicone adhesive 7-4202 (59.1 wt.-% in ethyl acetate) and 34.6 g of silicone adhesive 7-4302 (60.9 wt.-% in ethyl acetate) were added and shortly stirred. Then, 10.3 g rotigotine of polymorphic Form II were added to the mixture while stirring. The final mixture was stirred until a homogenous dispersion was obtained.

Preparation of the Final TTS (Step 2)

The final patches of Example 9 were manufactured according to the method described in Step 3 of Example 3, but without adding a skin adhesive layer.

Instead of coating reservoir layers each having a coating weight of 75 g/m² and laminating two coated layers together to achieve the final coating weight of 150 g/m², the coating of only one reservoir layer having a coating weight of 150 g/m² is also possible.

Comparative Example 2

Single-day mono-layer TTS comprising a reservoir layer having a coating weight of 50 g/m² and containing 9 wt.-% rotigotine and 4 wt.-% PVP; solvent system used for the preparation method: heptane/ethanol (1.4:1 (w/w))

Comparative Example 2 corresponds to Comparative Example 1, except for the use of rotigotine of polymorphic Form II instead of rotigotine of polymorphic Form I as starting material and an increased PVP content resulting in a rotigotine to PVP wt.-% ratio of 9:4.

Comparative Example 3

7-Day mono-layer TTS comprising a reservoir layer having a coating weight of 150 g/m² and containing 18 wt.-% rotigotine and 8 wt.-% PVP; solvent system used for the preparation method: heptane/ethanol (1:1.5 (w/w))

Preparation of the Reservoir Layer Matrix (Step 1)

11.0 g of rotigotine of polymorphic Form II and 7.9 g ethanol were added to 21.5 g of an ethanolic PVP solution (containing 22.7 wt.-% polyvinylpyrrolidone (Kollidon 90F), 0.1 wt.-% aqueous sodium metabisulfite solution (10 wt.-%), 0.1 wt.-% ascorbylpalmitate and 0.3 wt.-% DL-alpha-tocopherol). The mixture was stirred for 1.5 h at 60° C. Then, 30.5 g of silicone adhesive 7-4201 (73.6 wt.-% in heptane) and 30.7 g of silicone adhesive 7-4301 (73.3 wt.-% in heptane) were added and the mixture was stirred without heating until a homogenous dispersion was obtained.

Preparation of the Final TTS (Step 2)

The final patches of Comparative Example 2 were manufactured according to the method described in Step 3 of Example 3, but without adding a skin adhesive layer.

The respective compositions of Examples 3-9 and Comparative Examples 2 and 3 are summarized in Table 5.

TABLE 5

Composition of the patches of Examples 3-9 and Comparative Examples 2 and 3

| | Ingredient [mg/10 cm²], except stated otherwise | Comp. Ex. 2 | Ex. 3 | Ex. 4 Ex. 8 Ex. 9 Comp. Ex. 3 | Ex. 5 Ex. 6 | Ex. 7 |
|---|---|---|---|---|---|---|
| Reservoir layer | Rotigotine (Form II*) | 4.5 | 27.0 | 27.0 | 27.0 | 18.0 |
| | Rotigotine (Form II*) content [wt.-%] | 9.0 | 18.0 | 18.0 | 9.0 | 18.0 |
| | PVP | 2.0 | 12.0 | 12.0 | 12.0 | 8.0 |
| | PVP content [wt.-%] | 4.0 | 8.0 | 8.0 | 4.0 | 8.0 |
| | Rotigotine:PVP ratio [wt.-%] | 9:4 | 18:8 | 18:8 | 9:4 | 18:8 |
| | Silic. adhesive 7-430x | 21.74 | 55.39 | 55.39 | 130.39 | 36.928 |
| | Silic. adhesive 7-420x | 21.73 | 55.39 | 55.39 | 130.39 | 36.928 |
| | Sodium metabisulfite | 0.00045 | 0.005 | 0.005 | 0.005 | 0.004 |
| | Ascorbyl palmitate | 0.01 | 0.060 | 0.060 | 0.060 | 0.040 |
| | DL-α-Tocopherol | 0.025 | 0.150 | 0.150 | 0.150 | 0.100 |
| | Coating weight [g/m²] | 50.0 | 150.0 | 150.0 | 300.0 | 100.0 |
| Skin adhesive layer | Rotigotine (Form II*) | — | — | — | — | 9.0 |
| | Rotigotine (Form II*) content [wt.-%] | — | — | — | — | 9.0 |
| | PVP | — | — | — | — | 4.0 |
| | PVP content [wt.-%] | — | — | — | — | 4.0 |
| | Rotigotine:PVP ratio [wt.-%] | — | — | — | — | 9:4 |
| | Silic. adhesive 7-430x | — | 10.8 | — | — | 43.464 |
| | Silic. adhesive 7-420x | — | 7.2 | — | — | 43.464 |
| | Sodium metabisulfite | — | — | — | — | 0.0018 |
| | Ascorbyl palmitate | — | — | — | — | 0.020 |
| | DL-α-Tocopherol | — | — | — | — | 0.050 |
| | Coating weight [g/m²] | — | 18.0 | — | — | 100.0 |

*For the preparation of the respective example patches rotigotine of polymorphic Form II was used as starting material. The final patches contain rotigotine in non-crystalline form.
X = 1 for silicone adhesive in heptane
X = 2 for silicone adhesive in ethyl acetate In Table 6, the composition and selected physical properties of the dispersions forming the drug containing self-adhesive matrix layer of representative example patches are shown. The dispersions were prepared in accordance with the methods described in Example 3 as well as Comparative Example 3 and were investigated in the liquid state before laminating them and before the solvents were evaporated in a drying step. The self-adhesive matrix layer of the transdermal therapeutic system described herein represents a dispersion of rotigotine/PVP droplets in a matrix of silicone adhesives and can therefore be considered as a non-aqueous emulsion. From the data shown in Table 6, it becomes apparent that the use of an ethyl acetate/ethanol solvent mixture, in contrast to a heptane/ethanol solvent mixture, leads to physically stable emulsions also at high concentrations of rotigotine in the inner and the outer phase of the emulsion (cf. Example 3 in comparison to Comparative Example 3).

TABLE 6

Solvents and selected physical properties of the dispersions (i.e. non-aqueous emulsions) forming the self-adhesive matrix layer of the TTS of Example 3 as well as Comparative Example 3

| Example[1]/ Solvent system | API:PVP %-ratio | Outer Phase[2] (PVP) | Drug conc. [wt.-%] Phase[2] (silic. adhes.) | API conc. | Inner/outer phase ratio Density (23° C.) | Droplet size Inner phase | Remark |
|---|---|---|---|---|---|---|---|
| Ex. 3 EtAC:EtOH 5:1 | 18:8 | 33.0 | 2.4 | 13.8 | 0.947 | <35 μm | stable |
| Comp. Ex. 3 Heptane:EtOH 1:1.5 | 18:8 | 25.1 | 1.3 | 19.3 | 0.919 | <20 μm | Instable[3] |

API = Rotigotine
[1]The dispersions forming the self-adhesive matrix layer of the transdermal therapeutic systems of Example 3 as well as Comparative Example 3 were prepared in accordance with the methods described in the respective examples and were investigated in the liquid state before laminating them and before the solvents were evaporated in a drying step.
[2]Inner and outer phase were separated by centrifugation; drug content was determined in each phase by HPLC
[3]Crystallization of rotigotine was observed at room temperature after a storage/holding time of 2 days at room temperature Surprisingly, it was found that the solubility of PVP in ethyl acetate is enhanced by rotigotine by one order of magnitude. That is, rotigotine apparently functions as a co-solvent for PVP in an aprotic polar solvent such as ethyl acetate. This indicates that rotigotine forms an adduct with the PVP polymer and reveals a different solubility in dipolar organic solvents on the one hand and in a heptane/ethanol mixture on the other hand. Furthermore, the addition of a small portion of ethanol to ethyl acetate enables the formation of rotigotine/PVP droplets in ethyl acetate-based silicone adhesive solutions and allows for homogenously dispersing the rotigotine/PVP conjugate in the silicone adhesive solution at room temperature.

In Vitro Drug Permeation Testing Across an Ethylene Vinyl Acetate (EVA) Membrane In vitro Drug release was evaluated by a membrane permeation test performed over an extended period of time using a 51 μm thick membrane consisting of an ethylene vinyl acetate (EVA) copolymer with 9% vinyl acetate (CoTran™ Membrane, 3M) and the Paddle over Disk apparatus described in the United States Phamacopeia (USP). Phosphate buffer pH 4.5 was used as acceptor medium (900 ml; 32° C.; 50 rpm). The drug permeation rates into the acceptor medium were determined in regular intervals using a validated UV photometric or HPLC method.

In Vitro Drug Release Testing

The drug release test was performed under equivalent conditions as described for the drug permeation test, but without placing an EVA membrane between the release surface of the respective TTS and the acceptor medium. The cumulative amount of drug released into the acceptor medium was determined in regular intervals using a validated HPLC method.

Results—In Vitro Drug Permeation Across an EVA Membrane

Figure 6:
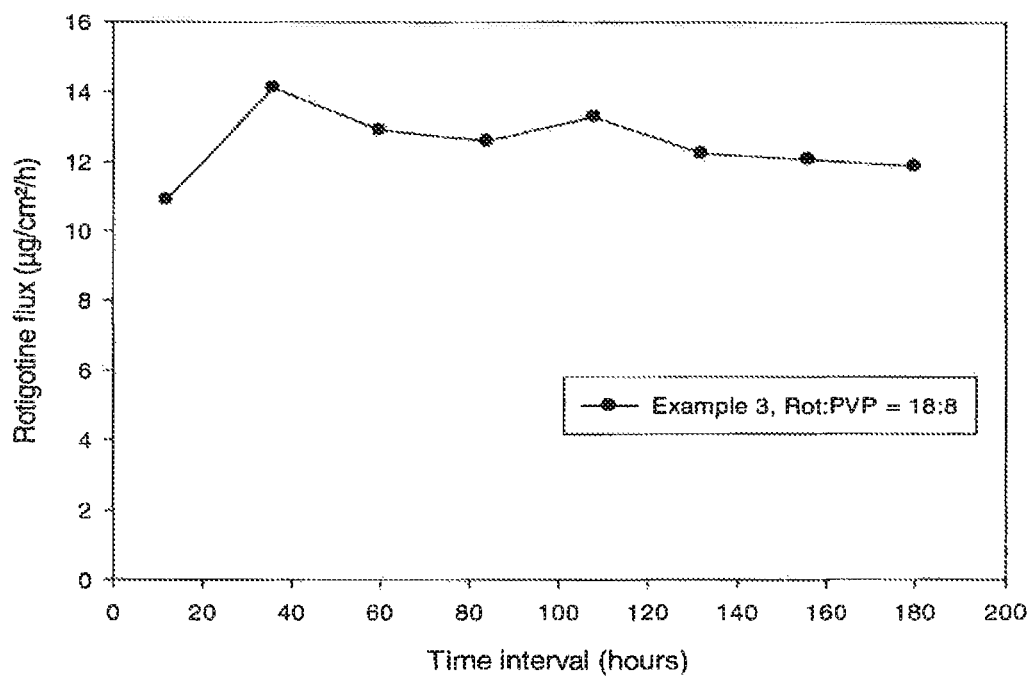
FIG. 6 shows the membrane permeation profile of the 7-day bi-layer TTS of Example 2.

The results of the EVA membrane tests performed with sample patches of Example 3 are depicted in FIG. 6.

The data show a constant drug permeation profile for the TTS of Example 3 over 7 days without any significant decline over the entire test period.

Figure 7:
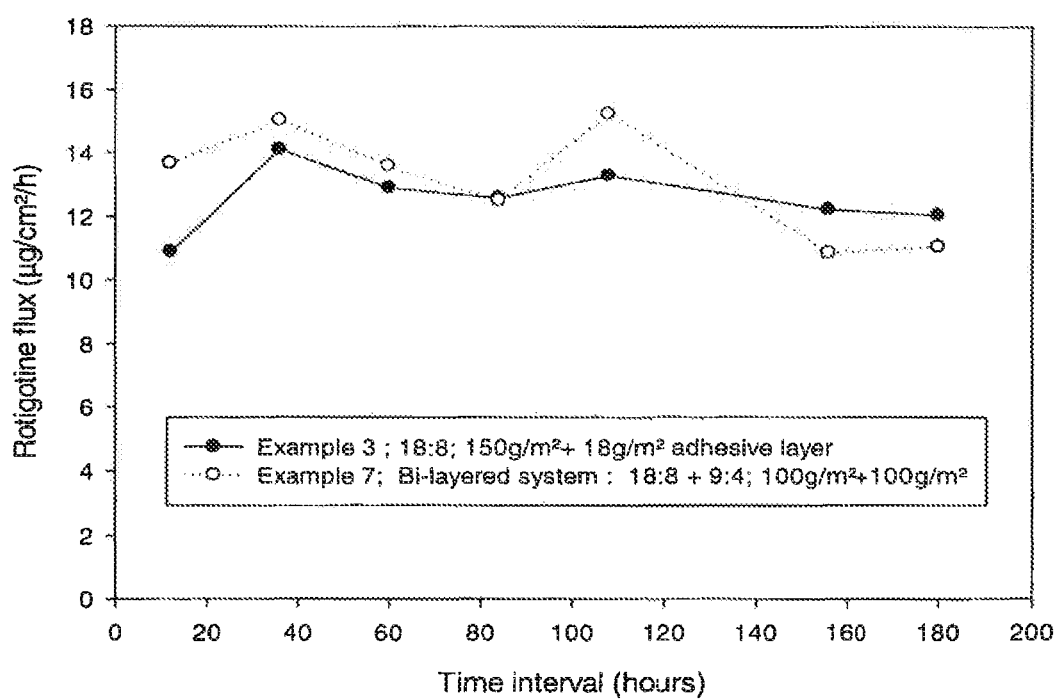
FIG. 7 shows the membrane permeation profile of the 7-day bi-layer TTS of Example 2 in comparison to the 7-day bi-layer TTS of Example 6.

The results of the EVA membrane tests performed with sample patches of Examples 3 and 7 are depicted in FIG. 7.

The data show constant and comparable drug permeation profiles for the TTS of Example 3 and the TTS of Example 7 over 7 days without any significant decline over the entire test period.

In comparison to the TTS of Example 3 comprising a skin adhesive layer containing no rotigotine, the initial flux rate was higher for the TTS, i.e. the gradient system, of Example 7. That is, a gradient system according to Example 7 offers the possibility of slightly increased drug absorption immediately after application.

Figure 8:
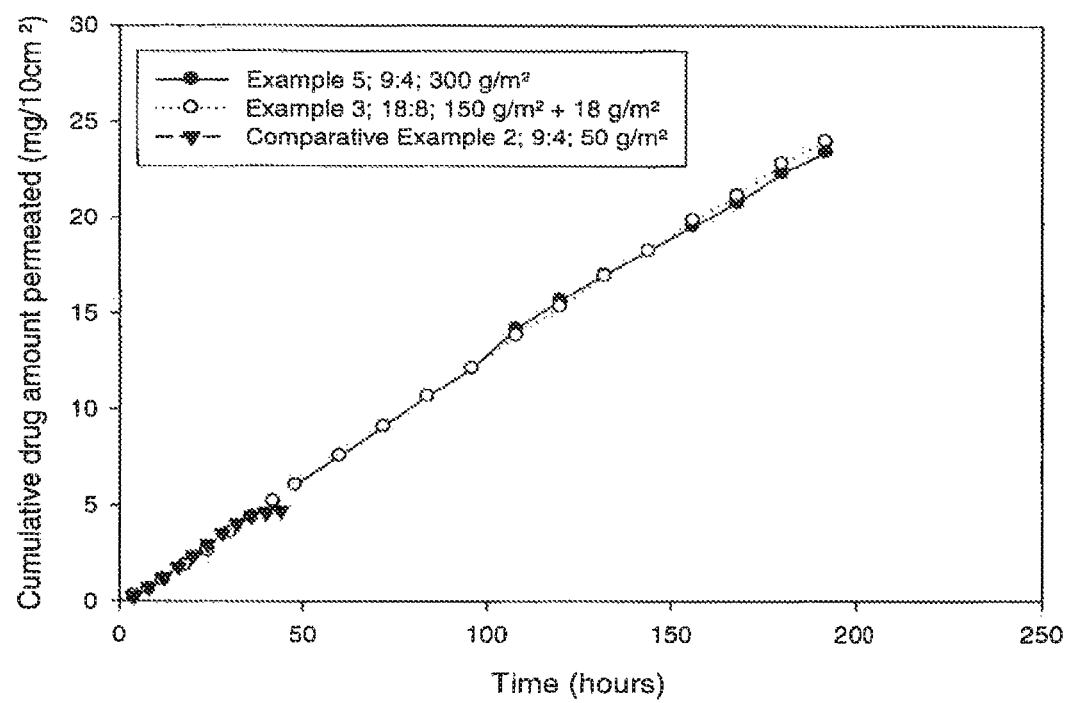
FIG. 8 shows the cumulative permeation profile of the 7-day bi-layer TTS of Example 2 and the 7-day mono-layer TTS of Example 4 in comparison to the 1-day TTS of Comparative Example 2.

In FIG. 8, the cumulative permeation profiles of the 7-day bi-layer TTS of Example 3, the 7-day mono-layer TTS of Example 5, and the 1-day TTS of Comparative Example 2 are depicted.

The data demonstrate that a prolongation of the functional life time of a TTS can be obtained by (a) increasing the thickness/coating weight of the self-adhesive matrix layer from 50 to 300 g/m$^2$ (Example 5) without changing the 9:4 wt.-% ratio of rotigotine to PVP known from Comparative Example 2 or (b) with a bi-layer self-adhesive matrix comprising a reservoir layer having a coating weight of 150 g/m$^2$ containing rotigotine and PVP in a wt.-% ratio of 18:8 and a skin adhesive layer having a coating weight of 18 g/m$^2$ containing no rotigotine.

Results—In Vitro Drug Release into an Acceptor Medium

Figure 9:
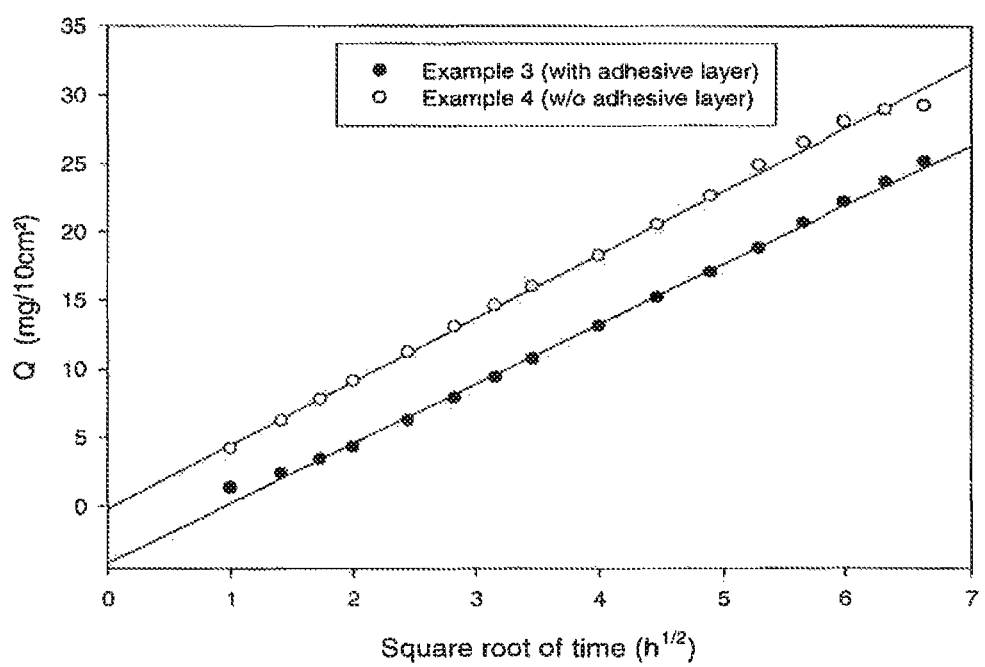
FIG. 9 shows the cumulative release (Q) of rotigotine from the 7-day bi-layer TTS of Example 2 comprising a skin adhesive layer in comparison to the 7-day mono-layer TTS of Example 3 comprising no skin adhesive layer.

In FIG. 9, the cumulative release (Q) of rotigotine from the 7-day bi-layer TTS of Example 3 and the 7-day monolayer TTS of Example 4 is depicted. The patches of Examples 3 and 4 both comprise a reservoir layer having an identical composition and only differ in that the patch of Example 3 further comprises a skin adhesive layer containing no rotigotine.

The data show that the drug release from the patches of Examples 3 and 4 in both cases follows a typical square root of time kinetics up to a drug depletion rate of more than 80% related to the total drug content of the reservoir layer. The slope of the regression lines is very similar and the onset of the release is only slightly delayed by the skin adhesive layer of the patch of Example 3 having a coating weight of 18 g/m². That is, adhesion properties as well as the initial burst of the drug release can be adapted by a skin adhesive layer in accordance with drug safety needs and without compromising the release performance of a corresponding TTS.

The invention claimed is:

1. A multi-day transdermal therapeutic system, comprising
   (a) a backing layer,
   (b) a solvent-based self-adhesive matrix layer containing rotigotine as active ingredient, and
   (c) a release liner,
   wherein
      the self-adhesive matrix layer has a coating weight of about 150-400 g/m², and comprises a reservoir layer containing an amount exceeding 9 wt % and up to 25 wt.-% of rotigotine based on the weight of the reservoir layer,
      the transdermal therapeutic system is prepared by a method wherein a solvent system consisting of an aprotic polar solvent and a protic polar solvent is used,
      the transdermal therapeutic system contains sufficient rotigotine to administer a therapeutically effective amount of rotigotine for more than 3 days,
      the rotigotine does not crystallize during a 2 day storage at room temperature and
      the reservoir layer further contains polyvinylpyrrolidone ("PVP") and the rotigotine to polyvinylpyrrolidone weight ratio in the layer is 9:2 to 9:5 or multiples thereof,
      a non-crystalline form of rotigotine is reversibly associated with the PVP thereby forming distinct microreservoir particulates and said matrix layer does not contain particulates other than said microreservoir particulates comprising said PVP and the rotigotine associated therewith.

2. The transdermal therapeutic system according to claim 1, wherein the reservoir layer contains an amount exceeding 9 wt % and up to 20 wt.-% rotigotine based on the weight of the reservoir layer.

3. The transdermal therapeutic system according to claim 1, wherein the reservoir layer has a coating weight of about 250 to 400 g/m² or contains about 15.75 to 25 wt.-% rotigotine based on the weight of the reservoir layer, and wherein free rotigotine is molecularly dispersed in the self-adhesive matrix layer.

4. The transdermal therapeutic system according to claim 1, wherein the self-adhesive matrix layer further comprises a silicone skin-adhesive layer disposed between a reservoir layer within the matrix layer and the release liner and the skin-adhesive layer has a coating weight of about 10-150 g/m², and the matrix layer does not comprise acrylate-based polymer adhesive.

5. The transdermal therapeutic system according to claim 3, wherein the self-adhesive matrix layer further comprises a skin-adhesive layer comprising adhesive consisting of silicone disposed between the matrix layer and the release liner and the skin-adhesive layer has a coating weight of about 15-50 g/m² skin-adhesive.

6. The transdermal therapeutic system according to claim 3, wherein the transdermal system contains about 10-32 mg rotigotine/10 cm² surface of the self-adhesive matrix layer.

7. The transdermal therapeutic system according to claim 1, wherein the reservoir layer further comprises polyvinylpyrrolidone and the rotigotine to polyvinylpyrrolidone weight ratio is 9:4.

8. The transdermal therapeutic system according to claim 4, wherein the reservoir layer and the skin-adhesive layer each contain at least one or two amine-resistant silicone pressure sensitive adhesives, and the skin-adhesive layer has a coating weight of about 50 to 150 g/m² skin-adhesive.

9. A kit comprising two transdermal therapeutic systems according to claim 1, wherein the two transdermal therapeutic systems have the same or a different rotigotine content.

10. The transdermal therapeutic system according to claim 3, wherein the reservoir layer contains about 15.75 to 25 wt.-% rotigotine based on the weight of the reservoir layer.

11. The transdermal therapeutic system according to claim 10, wherein the reservoir layer contains about 18 to 25 wt % rotigotine based on the weight of the reservoir layer and has a coating weight of about 100-400 g/m².

12. The transdermal therapeutic system according to claim 1, wherein the transdermal system contains about 27 mg rotigotine/10 cm² surface of the self-adhesive matrix layer.

13. A transdermal therapeutic system according to claim 4, wherein one or more of the reservoir layer and the skin-adhesive layer contain a mixture of at least one high tack and at least one medium tack silicone pressure sensitive adhesive.

14. A transdermal therapeutic system according to claim 1, wherein the aprotic polar solvent and the protic polar solvent are present in a 2:1 to 9:1 ratio, and the reservoir layer comprises polyvinylpyrrolidone and the rotigotine forms an adduct with the polyvinylpyrrolidone.

15. A multi-day transdermal therapeutic system comprising
   (a) a backing layer,
   (b) a self-adhesive matrix layer, and
   (c) a release liner,
   wherein
      (i) the self-adhesive matrix layer has a coating weight of about 100-400 g/m² and comprises a reservoir layer comprising pressure sensitive adhesive consisting of a first silicone adhesive, optionally in a blend or copolymer with adhesive selected from the group consisting of a second silicone adhesive, styrenic polymer and polyisobutylene,
      and a skin adhesive layer disposed between the reservoir layer and the release liner,
      (ii) the reservoir layer contains
         (1) about 15.75-25 wt.-% rotigotine based on the weight of the reservoir layer and
         (2) about 5.25 to 13.9 wt % of polyvinylpyrrolidone,
      (iii) the rotigotine to polyvinylpyrrolidone weight ratio is 9:2 to 9:5,
      (iv) free rotigotine is molecularly dispersed in the self-adhesive matrix layer and a non-crystalline form of rotigotine is reversibly associated with the polyvinylpyrrolidone thereby forming distinct microreservoir particulates, and (v) the rotigotine does not crystallize during a 2 day storage at room temperature and the transdermal therapeutic system contains sufficient rotigotine to administer a therapeutically effective amount of rotigotine for more than 3 days and said matrix layer does not contain particulates other than the microreservoir particulates comprising polyvinylpyrrolidone and the rotigotine associated therewith.

16. A transdermal therapeutic system according to claim 1, wherein said system exhibits a C max that is 126% in comparison to a daily administration of a comparable single-day patch.

17. A transdermal therapeutic system according to claim 1, wherein the system supplies a bioequivalent rotigotine plasma concentration of a single-day system, yet contains approximately 0.4 mg/10 cm$^2$/day less rotigotine than said single-day system.

18. A transdermal therapeutic system according to claim 1, wherein the system further comprises polyvinylpyrrolidone; the aprotic polar solvent is ethyl acetate, the protic polar solvent is ethanol and the reservoir layer comprises microreservoir droplets formed from polyvinylpyrrolidone and rotigotine having a mean diameter that is 1.75 times larger than and containing about 32% more rotigotine than microreservoirs droplets present in a comparable transdermal therapeutic system prepared by a method wherein a solvent system consisting of heptane and ethanol is used.

19. The transdermal therapeutic system according to claim 4, wherein the silicone skin-adhesive layer does not comprise polyvinyl pyrrolidone.

20. The transdermal therapeutic system according to claim 15, wherein the skin-adhesive layer comprises from 5 to 10 wt % rotigotine.

21. The transdermal therapeutic system according to claim 4, wherein the skin-adhesive layer has a coating weight of about 100 to 150 g/m$^2$ skin-adhesive.

22. The transdermal therapeutic system according to claim 1, wherein the self-adhesive matrix layer comprises microreservoir particulates formed from a non-crystalline form of rotigotine reversibly associated with the PVP, but does not comprise acrylate-based polymer adhesive and does not contain particulates other than the microreservoir particulates.

23. A multi-day transdermal therapeutic system comprising
(a) a backing layer;
(b) a matrix layer and optional skin adhesive layer comprising rotigotine in a pressure sensitive adhesive consisting of a first silicone adhesive, optionally in a blend or copolymer with a second silicone adhesive; and
(c) a release liner;
wherein the matrix layer further comprises polyvinylpyrrolidone (PVP) and has a coating weight of about 250-400 g/m$^2$ or contains about 15.75-25 wt.-% rotigotine based on the weight of the matrix layer, free rotigotine is molecularly dispersed in the self-adhesive matrix layer and a non-crystalline form of rotigotine is reversibly associated with the PVP thereby forming distinct microreservoir particulates,
the transdermal therapeutic system contains sufficient rotigotine to administer a therapeutically effective amount of rotigotine for at least 4 days,
and said matrix layer does not contain particulates other than the microreservoir particulates comprising polyvinylpyrrolidone and the rotigotine associated therewith,
and the rotigotine to polyvinylpyrrolidone weight ratio in the layer is 9:2 to 9:5 or multiples thereof.

24. A transdermal therapeutic system comprising
(a) a backing layer,
(d) a solvent-based self-adhesive matrix layer containing rotigotine as active ingredient, and
(e) a release liner,
wherein the self-adhesive matrix layer comprises a reservoir layer, the reservoir layer has a coating weight of 300 g/m$^2$ and contains 9 wt % rotigotine or 18 wt % rotigotine based on the weight of the reservoir layer, and
the reservoir layer further contains polyvinylpyrrolidone and the rotigotine to polyvinylpyrrolidone weight ratio in the layer is 9:2 to 9:5 or multiples thereof,
a non-crystalline form of rotigotine reversibly associates with the polyvinylpyrrolidone thereby forming distinct microreservoir particulates,
and said reservoir layer does not contain particulates other than the microreservoir particulates comprising polyvinylpyrrolidone and the rotigotine associated therewith.

25. A multi-day transdermal therapeutic system, comprising
a) a backing layer,
b) a self-adhesive matrix layer containing distinct microreservoir particulates comprising rotigotine reversibly associated with polyvinylpyrrolidone, and
c) a release layer,
wherein
the matrix layer contains a rotigotine to polyvinylpyrrolidone weight ratio of 9:2 to 9:5 or multiples thereof,
the transdermal therapeutic system contains rotigotine in either an amount exceeding 9 wt % or at a coating weight of 200 to 400 g/m$^2$ which is sufficient to administer a therapeutically effective amount of rotigotine for more than 3 days,
and said matrix layer does not contain particulates other than the microreservoir particulates comprising polyvinylpyrrolidone and the rotigotine associated therewith.

26. The transdermal therapeutic system according to claim 25, wherein the self-adhesive matrix layer does not comprise acrylate-based polymer adhesive.

27. The transdermal therapeutic system according to claim 26, wherein the transdermal therapeutic system contains sufficient rotigotine to administer a therapeutically effective amount of rotigotine for 7 days or more.

* * * * *